US006565749B1

(12) United States Patent
Hou et al.

(10) Patent No.: US 6,565,749 B1
(45) Date of Patent: May 20, 2003

(54) MICROORGANISM FILTER AND METHOD FOR REMOVING MICROORGANISM FROM WATER

(75) Inventors: Kenneth C. Hou, West Chester, OH (US); Donald S. Bretl, West Chester, OH (US); Richard D. Hembree, Edina, MN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/628,632

(22) Filed: Jul. 31, 2000

Related U.S. Application Data

(63) Continuation-in-part of application No. 09/358,342, filed on Jul. 21, 1999, now abandoned.

(51) Int. Cl.[7] .............................................. B01D 71/56

(52) U.S. Cl. ............................ 210/500.38; 210/500.37; 210/490; 210/321.77; 210/321.86; 210/263; 210/502.1; 210/508; 210/644

(58) Field of Search ...................... 210/500.37, 500.38, 210/507, 508, 500.27, 490, 321.6, 321.77, 502.1, 263, 321.86, 644

(56) References Cited

U.S. PATENT DOCUMENTS

| | | |
|---|---|---|
| 3,242,073 A | 3/1966 | Guebert et al. |
| 3,278,560 A | 10/1966 | Gaertner |
| 3,314,897 A | 4/1967 | Gaertner |
| 3,352,424 A | 11/1967 | Guebert et al. |
| 3,591,010 A | 7/1971 | Pall et al. |
| 3,678,098 A | 7/1972 | Lewis et al. |
| 3,686,151 A | 8/1972 | Keim |
| 3,700,623 A | 10/1972 | Keim |
| 3,784,649 A | 1/1974 | Buckman et al. |
| 3,871,950 A | 3/1975 | Hashino et al. |

(List continued on next page.)

FOREIGN PATENT DOCUMENTS

| | | |
|---|---|---|
| EP | 0 798 003 | 10/1997 |
| WO | WO 97/38941 | 10/1997 |
| WO | WO 98/04335 | 2/1998 |
| WO | WO 00/35559 | 6/2000 |
| WO | WO 00/37385 | 6/2000 |

OTHER PUBLICATIONS

CUNO Process Filtration Products, Product Information, Zeta Plus VIROSORB® 1MDS, 6 pages(1989).

Daniels, S., The Adsorption of Microorganisms onto Solid Surfaces: A Review, *Developments in Industrial Microbiology*, vol. 13, Proceedings of the Twenty–Eighth General Meeting of the Society for Industrial Microbiology, Aug. 29–Sep. 4, 1971, pp. 211–243.

(List continued on next page.)

*Primary Examiner*—Ana Fortuna
(74) *Attorney, Agent, or Firm*—Richard L. Alexander; James C. Vago; Carl J. Roof

(57) ABSTRACT

A filter for removing microorganisms from a fluid is provided by the invention. The filter includes a substrate having a reactive surface, and a polymer covalently bonded to the reactive surface of the substrate. The polymer includes a plurality of cationic groups for attracting microorganisms. Faucet mounted filters and pour through filters containing the polymer coated substrate are provided. Also disclosed are methods for using and manufacturing filters for removing microorganisms from a fluid.

26 Claims, 6 Drawing Sheets

U.S. PATENT DOCUMENTS

| | | | | |
|---|---|---|---|---|
| 3,898,188 | A | | 8/1975 | Rembaum et al. |
| 4,007,114 | A | | 2/1977 | Ostreicher |
| 4,181,694 | A | | 1/1980 | Hashino et al. |
| 4,190,532 | A | | 2/1980 | Halbfoster |
| 4,292,417 | A | | 9/1981 | Ishii et al. |
| 4,305,782 | A | | 12/1981 | Ostreicher et al. |
| 4,309,247 | A | | 1/1982 | Hou et al. |
| 4,321,288 | A | | 3/1982 | Ostreicher |
| 4,340,479 | A | | 7/1982 | Pall |
| 4,340,480 | A | | 7/1982 | Pall et al. |
| 4,352,884 | A | | 10/1982 | Nakashima et al. |
| 4,361,486 | A | | 11/1982 | Hou et al. |
| 4,366,068 | A | | 12/1982 | Ostreicher et al. |
| 4,399,035 | A | | 8/1983 | Nohmi et al. |
| 4,473,474 | A | | 9/1984 | Ostreicher et al. |
| 4,523,995 | A | * | 6/1985 | Pall et al. |
| 4,578,150 | A | | 3/1986 | Hou |
| 4,645,567 | A | | 2/1987 | Hou et al. |
| 4,673,504 | A | * | 6/1987 | Ostreicher et al. |
| 4,704,324 | A | | 11/1987 | Davis et al. |
| 4,708,803 | A | | 11/1987 | Ostreicher et al. |
| 4,722,964 | A | | 2/1988 | Chan et al. |
| 4,734,208 | A | | 3/1988 | Pall et al. |
| 4,769,148 | A | | 9/1988 | Fibiger et al. |
| 4,778,596 | A | * | 10/1988 | Linder et al. |
| 4,859,340 | A | | 8/1989 | Hou et al. |
| 4,915,839 | A | | 4/1990 | Marinaccio et al. |
| 4,981,591 | A | | 1/1991 | Ostreicher |
| 4,983,288 | A | | 1/1991 | Karbachsch et al. |
| 4,983,717 | A | | 1/1991 | Yamasaki et al. |
| 5,017,292 | A | | 5/1991 | DiLeo et al. |
| 5,035,802 | A | | 7/1991 | Yamasaki et al. |
| 5,106,500 | A | | 4/1992 | Hembree et al. |
| 5,133,878 | A | | 7/1992 | Gisell et al. |
| 5,183,607 | A | | 2/1993 | Beall et al. |
| 5,238,570 | A | | 8/1993 | Hugl et al. |
| 5,268,093 | A | | 12/1993 | Hembree et al. |
| 5,328,613 | A | | 7/1994 | Beall et al. |
| D358,868 | S | | 5/1995 | Hembree et al. |
| 5,525,214 | A | | 6/1996 | Hembree |
| 5,536,394 | A | | 7/1996 | Lund et al. |
| 5,543,054 | A | * | 8/1996 | Charkoudian et al. |
| D377,388 | S | | 1/1997 | Weber et al. |
| D377,515 | S | | 1/1997 | Hembree et al. |
| 5,620,790 | A | | 4/1997 | Holzki et al. |
| 5,709,794 | A | | 1/1998 | Emmons et al. |
| 5,804,280 | A | | 9/1998 | Pall et al. |
| 5,855,788 | A | | 1/1999 | Everhart et al. |
| 6,045,694 | A | * | 4/2000 | Wang et al. |

OTHER PUBLICATIONS

Dorfner, K, "2.1—Synthetic Resin Ion Exchangers," *Ion Exchangers Properties and Applications*, Cover page and pp. 16–35 (1972).

Gerba, C.P., "Applied and Theoretcial Aspects of Virus Adsorption to Surfaces," *Advances in Applied Microbiology*, vol. 30, pp. 133–168 (Copyright © 1984).

Gerba, C.P., Et Al, "Removal of Poliovirus and Rotavirus from Tapwater by a Quaternary Ammonium Resin," *Water Res.*, vol. 18, No. 1, pp. 17–19 (1984).

Goyal, S.M., Et Al., "Concentration of Bacteriophage Lysates by Filter Chromatography," *Journal of Virological Methods*, vol. 1, pp. 79–85 (1980).

Goyal, S.M., Et Al., "Simple Method for Concentration of Bacteria from Large Volumes of Tap Water," *Applied and Environmental Microbiology*, vol. 40, No. 5, pp. 912–916 (Nov. 1980).

Hercules Product Information, Hercules MSDS—KYMENE 450 wet strength resin, 4 pages (Jan. 29, 1998).

Hill, Jr., W.F., Et Al, "Detection of Virus in Water: Sensitivity of the Tentative Standard Method for Drinking Water," *Applied and Environmental Microbiology*, vol. 31, No. 2, pp. 254–261 (Feb. 1976).

Hou, K., Et Al, "Capture of Latex Beads, Bacteria, Endotoxin, and Viruses by Charge Modified Filters," *Applied and Environmental Microbiology*, vol. 40, No. 5, pp. 892–896 (Nov. 1980).

Hurst, C.J., Et Al., "Differential Effects of Tretrazolium Dyes upon Bacteriophage Plaque Assay Titers," *Applied and Environmental Microbiology*, vol. 60, No. 9, pp. 3462–3465 (Sep. 1994).

Isbister, J.D., Et Al., "Increasing ARCAT© Test Sensitivity for Examination of Potable Waters," *Project Summary*, United States Environmental Protection Agency, Research and Development, 3 pages (May 1982).

Ma, J., Et Al., "Evaluation of MK Filters for Recovery of Enteroviruses from Tap Water," *Applied and Environmental Microbiology*, vol. 60, No. 6, pp. 1974–1977 (Jun. 1994).

Moore, R.S., Et Al., "Improved methods for poliovirus recovery from water with electropositive adsorbent filters," *Annu. Meet. Am. Soc. Microbiol.*, paper Q55, 14 pages (1982).

Preston, D.R., Et Al., "Removal of Viruses from Tapwater by Fiberglass Filters Modified with a Combination of Cationic Polymers," *Wat. Sci. Tech.*, vol. 21, No. 3, pp. 93–98 (1989).

Sobsey, M.D., Et Al., "Improved Electopositive Filters for Concentrating Viruses from Large Volumes of Water," *Presented at the International Symposium on Viruses and Wastewater Treatment*, pp. 1–7 (Sep. 15–17, 1980).

Sobsey, M.D., Et Al., "Concentration of Poliovirus from Tap Water Using Positively Charged Microporous Filters," *Applied and Environmental Microbiology*, vol. 37, No. 3, pp. 588–595 (Mar. 1979).

United States Environmental Protection Agency, Registration Division, "Guide Standard and Protocol for Testing Microbiological Water Purifiers," Report of Task Force, pp. 1–41, submitted Apr. 1986 Revised Apr. 1987).

World Health Organization—Geneva, 1996 "Chapter 2—Microbiological aspects: introduction," *Guidelines for drinking–water quality, Second Edition, vol. 2, Health Criteria and other supporting information,* Cover page and pp. 9–12.

Zerda, K.S., Et Al., Adsorption of Viruses to Charge–Modified Silica, *Applied and Environmental Microbiology*, vol. 49, No. 1, pp. 91–95 (Jan. 1985).

* cited by examiner

MICROORGANISM FILTER AND METHOD FOR REMOVING MICROORGANISM FROM WATER

This application is a continuation-in-part of application Ser. No. 09/358,342, filed Jul. 21, 1999 now amended.

FIELD OF THE INVENTION

The invention relates to filters for removing microorganisms from liquid, methods for removing microorganisms from liquid, and methods for manufacturing filters. In particular, the invention relates to filter technology for the removal of bacteria and viruses from drinking water under conditions encountered in faucet mounted filters and pour through filters.

BACKGROUND OF THE INVENTION

Many filter designs are available for removing contaminants from drinking water. Exemplary designs are described by U.S. Pat. Nos. 5,709,794 to Emmons, et al.; 5,536,394 to Lund, et al.; 5,525,214 to Hembree; 5,106,500 to Hembree, et al.; and 5,268,093 to Hembree, et al. which were originally assigned to Recovery Engineering, Inc.

Several filter designs utilizing membrane technology have been proposed for removing submicron size microorganisms. For example, U.S. Pat. No. 5,017,292 to DiLeo, et al. describes a composite membrane including a porous membrane substrate, a surface skin having ultrafiltration separation properties, and an intermediate porous zone having an average pore size smaller than that of the substrate.

Chemical forces can be used to adhere microbials to solid surfaces. See Bitton and Marshall, "Adsorption of Micro organisms to Surfaces," John Wiley & Sons, New York, pages 1–57 and by Gerba C.P., "Applied and Theoretical Aspects of Virus Adsorption to Surfaces," Adv. Appl. Microbiol., vol. 30, pages 133–168 (1984). According to their discussion, charge interaction can be considered a major cause of interaction between virus and adsorbent surfaces. Most viruses have coats composed of protein polypeptides containing amino acids such as glutamic acid, aspartic acid, histidine and tyrosine. These amino acids contain carboxyl and amino groups which, upon ionization, give the viral capsid an electrical charge.

Based on the theory of charge interaction as means of removing micro organisms from the water, positively charged ion exchange resins have been utilized for bacteria adsorption by Daniels, "Developments In Industrial Microbiology", Vol. 13; Proceedings of the twenty-eighth General Meeting of the Society for Industrial Microbiology, pages 211–243 (1972). The fundamental framework of these ion exchange resins is an elastic three dimensional hydrocarbon network comprising ionizable groups, either cationic or anionic, chemically bonded to the backbone of a hydrocarbon framework. The network is normally fixed, insoluble in common solvents and chemically inert. The ionizable functional groups attached to the matrix carry active ions with counter-ions which can be exchanged by the other counter-ions existed in water. Typical examples of commercially available ion exchange resins are the poly styrene cross-linked with divinyl benzene (DVB), and the methacrylate copolymerized with DVB. In the case of polystyrene, a three dimensional network is formed first, and the functional groups are then introduced into benzene rings through chloromethylation. Since those ionizable groups are highly hydrophilic, the more the existence of those groups in resin structure, the more the resin will swell to restrict the flow of water. The resistance to flow exhibited by these resins in controlled by the degree of cross-linking usually in the range of 2 to 12% as discussed by K. Dorfner, "Ion Exchangers" Ann Arbor Science Publishers, Inc., pages 16–35, New York (1962). With a low degree of cross-linking, the hydrocarbon network is more easily stretched, the swelling is large, and the resin exchanges small ions rapidly and even permits relatively large ions to undergo exchange. Conversely, as the cross-linking is increased to make the structure more rigid for high liquid flow, the hydrocarbon matrix is less resilient, the pores in the resin network are narrowed, the exchange process is slower, and the exchanger resin increases its tendency to exclude large ions from entering the structure. The ion exchange resins made by cross-linking the functional group carrying polymers have been successfully applied for the removal of both organic and inorganic ions in Angstrom size range but they are normally unsuitable for the relatively large sized micro-organisms. Also, the matrix swells and the flow resistance increases due to the pore narrowing.

U.S. Pat. No. 4,361,486 to Hou, et al., describes a filter which can be used for removing soluble iron and manganese from an aqueous fluid, and for removing and inactivating microorganisms from fluids. The filter includes an amount of particulate including magnesium peroxide or calcium peroxide immobilized on a substantially inert porous matrix. The filter media can be provided with an electropositive potential by modifying the surface of the particulate or inert porous matrix with a surface modifying agent. Hou, et al., "Capture of Latex Beads, Bacteria, Endotoxin, and Viruses by Charge-Modified Filters," Appl. Environ. Microbiol., vol. 40, no. 5, pages 892–896, November 1980, reports the use of electropositive filters in removing microorganisms and other negatively charged particles from water. Charge modified filters are disclosed by U.S. Pat. Nos. 4,305,782 and 4,473,474 Ostreicher, et al.

U.S. Pat. No. 4,352,884 to Nakashima, et al. discloses a carrier for bioactive materials comprised of a substrate coated with a copolymer. The substrate may be one of various materials, including inorganic nature such as glass, activated carbon, silica, and alumina as well as organic polymers such as polystyrene, polyethylene, polyvinyl chloride, nylon, polyester, polymethyl methacrylate, and naturally occurring high polymers such as cellulose. The copolymer can be an acrylate or methacrylate monomer and a copolymerizable unsaturated carboxylic acid or unsaturated amine.

U.S. Pat. No. 3,898,188 to Rembawn, et al. and U.S. Pat. No. 3,784,649 to Buckman, et al. describe the polymerization of a dihalide and a ditertiary amine to form polyquaternary ammonium resin. These polymers have found utility as flocculants in the clarification of water supplies. The materials are also known to exhibit germicidal action or as an effective bactericidal and fungicidal agents.

Preston, D. R., et al., "Removal of Viruses from Tapwater by Fiberglass Filters Modified with a Combination of Cationic Polymers," Wat. Sci. Tech. Vol. 21, No. 3, pp 93–98 (1989) describes the development of an electropositive filter capable of adsorbing enteroviruses from water at pH 5 to 9. This article reports that electronegative fiberglass filters can be converted to electropositive filters by soaking the filters in an aqueous solution of a cationic polymer and allowing the treated filters to air dry. The cationic polymers polyethylenimine and Nalco cationic polymer 7111 can be used to produce a filter which can recover enteroviruses from environmental waters.

Faucet-mounted drinking water filters are described by U.S. Pat. No. 5,525,214. In general, faucet-mounted drinking filters include a filtration media for removing chemical and mineral contaminants as well as larger microorganisms. Common filter media include carbon, which is often in the form of a porous block. Additional contaminants, such as lead, can be removed with the addition of selective adsorbents. In addition, the filtration media commonly used in faucet-mounted drinking water filters have been combined with microfilters for the removal of small microorganisms and particles. The microfiltration is usually accomplished as a result of the fine porosity of the carbon block, or with the use of a second filter, including a hollow fiber membrane material.

SUMMARY OF THE INVENTION

A filter for removing microorganisms from a liquid is provided by the invention. The filter includes a microorganism filtration media including a substrate having a reactive surface and a polymer covalently bonded to the reactive surface of the substrate. The polymer includes a plurality of cationic groups for attracting microorganisms in a liquid. The filtration media exhibits an MS-2 virus removal coefficient in water of greater than 10 ml/g-sec.

The polymer which is covalently bonded to the substrate is preferably at least one of polyamide-polyamine polymer, polyamine polymer, and mixtures thereof. Exemplary polyamine and polyamide-polyamine polymers include those polymers having at least one of the following repeating units:

I

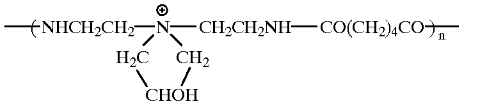

II

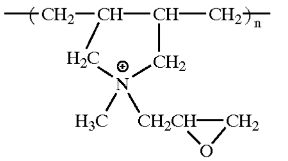

III

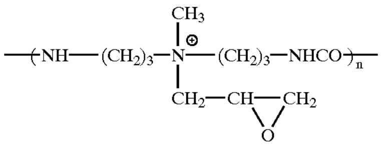

wherein n, for each of formulas I–III, is between about 10 and 100,000. The polymer preferably has a number average molecular weight of between about 25,000 and about 2,000,000, and more preferably between about 500,000 and 1,500,000. The polymer can be provided as a mixture of separate polymers including repeating units of any one or more of formulas I–III, or as copolymers containing repeating units of any one of formulas I–III or any combination of formulas I–III. Another polymer can include a reaction product of polyethylenimine and a cross-linking agent, such as, a di-epoxy cross-linking agent. The polyethylenimine polymer preferably has a repeating unit of the following formula:

$$-(CH_2-CH_2-NH)_n- \qquad \text{IV}$$

wherein n is between about 10 and about 1,000,000. The polyethylenimine polymer preferably has a number average molecular weight of between about 800 and about 1,000,000. The di-epoxy cross-linking agent is preferably a diglycidyl ether such as the diglycidyl ether of 1,4-butanediol.

Substrate is preferably a substrate having a surface which is capable of reacting with the polymer to provide a covalent bond between the substrate and the polymer. Preferably, the reactive surface of the substrate includes functional groups capable of reacting with reactive groups of the polymer, including epoxy groups and azetidinium groups. Exemplary functional groups which can be present on the substrate include hydroxyl groups, amino groups and hydrosulfyl groups. The substrate can be provided in the form of a fibrous material and/or particulate material. Preferred materials include glass, silica (including diatomaceous earth), alumina, polystyrene, polypropylene, polyethylene, polyvinyl alcohol, polyamide, cellulose, and mixtures thereof. A preferred substrate includes glass fiber web.

The filtration media includes a charge density of at least about 0.001 milli-equivalent/gram filtration media. In addition, the filtration media preferably exhibits an extractables of less than 20 ppm nitrogen in extracted water, wherein the extractables is determined by a Hach DR-700 colorimeter after soaking two grams of filtration media into 250 ml nitrogen free water for two hours at room temperature.

A method for removing microorganisms from water is provided by the invention. The method includes a step of reacting a polymer to a substrate surface to provide a filtration media exhibiting covalent bonding between the polymer and the substrate surface. The polymer includes a plurality of cationic groups for attracting microorganisms, and the filtration media exhibits an MS-2 virus removal coefficient in water of greater than 10 ml/g-sec. The method includes a step of passing water through the filtration media to remove microorganisms from the water.

A faucet mount filter is provided by the invention. The faucet mount filter includes a housing having an inlet, an outlet, and an interior region. The interior region contains a water treatment material. The water treatment material includes a filtration media having a substrate with a reactive surface and a polymer covalently bonded to the reactive surface of the substrate. The polymer includes a plurality of cationic groups for attracting microorganisms. The faucet mount filter includes a valve for controlling flow of water into the inlet of the housing, and an adapter for attaching the valve to a faucet.

A pour through filter is provided by the invention. The pour through filter includes a housing having an inlet, an outlet, and an interior region. The interior region includes a pleated filtration media. The pleated filtration media includes a substrate having a reactive surface and a polymer covalently bonded to the reactive surface. In addition, the polymer includes a plurality of cationic groups for attracting microorganisms in water. The interior region can additionally include a layer of microorganism filtration media in combination with the pleated microorganism filtration media. For example, the layer of microorganism filtration media can be provided around the pleated microorganism filtration media.

A method for manufacturing a microorganism filtration media is provided by the invention. The method includes steps of providing a substrate, such as, as glass fiber web, coating the substrate with a polymer, and heating the coated substrate to dry and covalently react the polymer to the substrate. The polymer is preferably at least one of polyamide-polyamine polymer, polyamine polymer, and mixtures thereof, and is preferably provided at a solids content of between about 0.1 wt. % and about 10 wt. %.

DETAILED DESCRIPTION OF THE INVENTION

Figure 1:
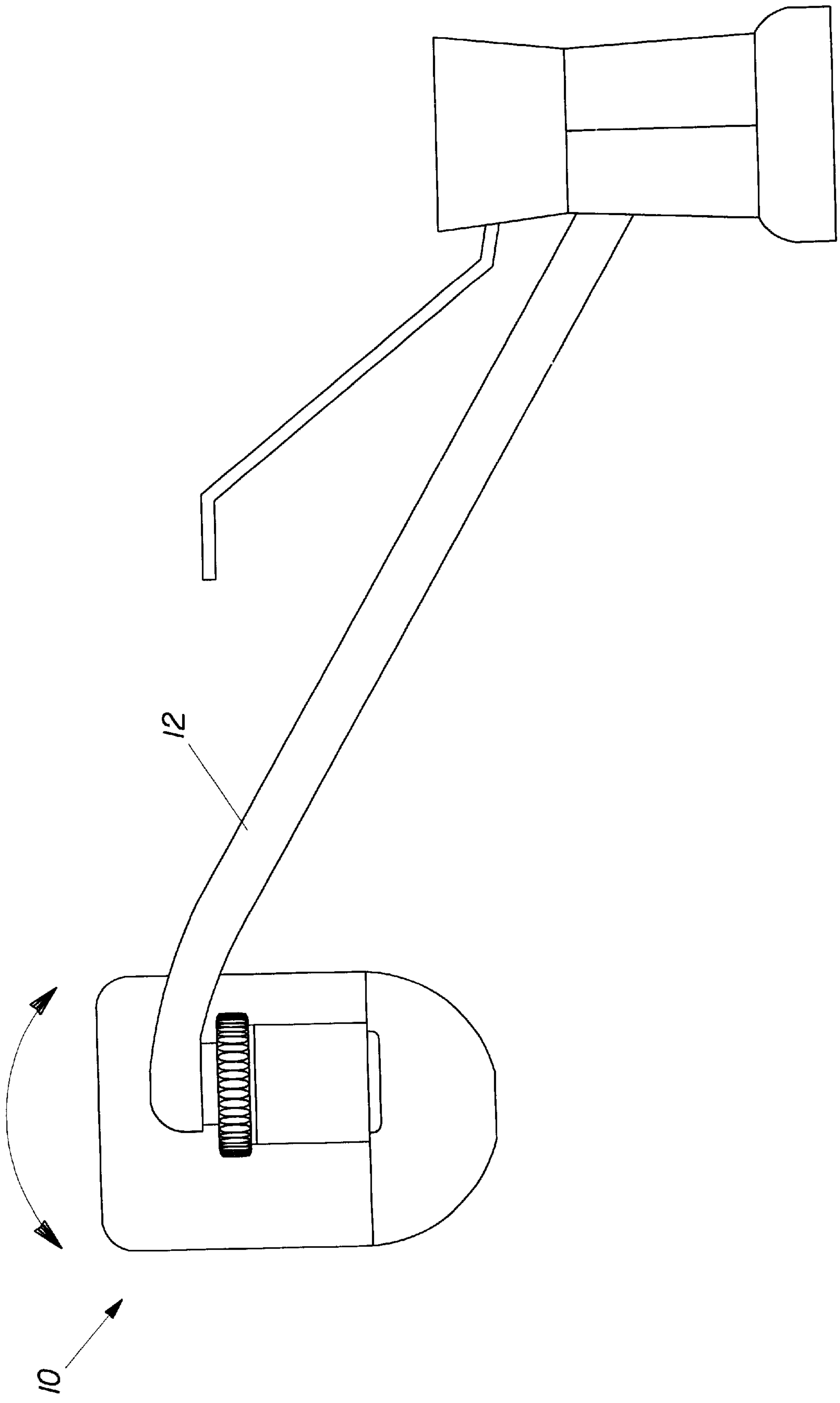
FIG. 1 is a perspective view of a faucet mount filter according to the principles of the invention.

The present invention relates to a filter which includes a microorganism filtration media for removing microorganisms including bacteria and viruses. When the filter is used for the filtration of water, it can be referred to as a water treatment material. The microorganism filtration media can be referred to herein as the filtration media, and can be used in combination with other components of a filter. Microorganisms generally have a size of less than about 1$\mu$. Conventional filters for use with drinking water typically remove contaminants having a size of 3$\mu$ or greater.

Microorganisms which can be removed by the filtration media of the invention include bacteria and viruses. Bacteria generally have a size between about 0.2$\mu$ and about 10$\mu$. Particular species of bacteria which are sometimes found in drinking water and which can be removed by the filter of the present invention include *E. coli, Salmonella typhi*, other salmonellae, Shigella spp., *Vibrio cholerae, Yersinia enterocolitica*, Legionella, *Pseudomonas aeruginosa*, Aeromonas spp., Mycobacterium, atypical, and mixtures thereof. Viruses typically have a size of between about 10 nm and about 200 nm. Viruses sometimes found in drinking water and which are of particular concern for removal therefrom by the filter of the invention include Adenoviruses, Enteroviruses, Hepatitis A, Hepatitis E, Norwalk virus, Rotavirus, Small round viruses (other than Norwalk virus), and mixtures thereof.

Most viruses have coats which include protein polypeptides that contain amino acids such as glutamic acid, aspartic acid, histidine, and tyrosine. In general, these amino acids contain weakly acidic and basic groups (i.e., carboxyl and amino groups), which ionize to provide the viral capsid with an electrical charge. In addition, each amino acid ionizing group in the polypeptide has a characteristic disassociation constant. The variation of disassociation constants among the various polypeptides ensures that most viruses have net charges that vary continuously with pH, and can be measured by iso-electric focusing and are expressed as iso-electric point (IEP).

Microorganism Filtration Media

The microorganism filtration media includes a porous substrate and a polymer composition covalently bonded to the substrate. The microorganism filtration media can be referred to as a polymer modified filtration media. The polymer modified filtration media allows liquid to flow therethrough. A preferred liquid which can be processed by the filter of the invention is water. The polymer composition is covalently bonded to the substrate and includes groups which adsorb microorganisms present in the liquid. As liquid flows through the microorganism filtration media, microorganisms are adsorbed by the groups provided on the polymer. Furthermore, the covalent bond between the polymer and the substrate provides reduced leaching of the polymer from the filter into the liquid compared with filters prepared without the covalent bonding as shown in Example 11.

The substrate is preferably a porous substrate having a surface which is reactive to the polymer composition. The substrate is preferably sufficiently porous to allow water to flow therethrough at desirable flow rates under the conditions of operation. It is expected that the presence of the polymer covalently bonded to the substrate will not significantly decrease the porosity of the substrate or flow rate of liquid through the substrate. That is, it is expected that the substrate which includes the polymer bonded thereto will provide a desirable degree of flow under the intended conditions of operation. In the case of a faucet mount applications, the flow rate of water through the faucet mount filter (which includes the filtration media) should be at least about one liter per minute under conditions of a water supply pressure of 60 psi or less and when the filtration media is provided within a volume of less than about one liter. In pour through applications, it is desirable for the filter cartridge (which includes the filtration media) to allow a water flow therethrough at a rate of at least about one liter per ten minutes under a head of six inches water (about 0.5 psi or less) when the filtration media is provided within a volume of less than about one liter.

The substrate preferably includes a surface which is capable of reacting with the polymer to provide a covalent bond between the substrate and the polymer. Preferably, the reactive surface of the substrate includes functional groups capable of reacting with reactive groups of the polymer, including epoxy groups and azetidinium groups. Exemplary functional groups on the reactive surface of the substrate include hydroxyl groups, amino groups, and hydrosulfyl groups. The substrate can be provided in the form of fibrous material and/or particulate material. Preferred materials include glass, silica (including diatomaceous earth), alumina, polystyrene, polypropylene, polyethylene, polyvinyl alcohol, polyamide, cellulose, and mixtures thereof.

In the case of a substrate prepared from fibers, it is preferable that the fibers have an average diameter of between about 0.2$\mu$ and about 25$\mu$. In addition, the substrate can include mixtures of different diameter size fibers. Exemplary substrates prepared from fibers include woven fabrics, unwoven fabrics, and knitted fabrics. In general, it is preferable that the substrate has an average pore size ranging from between about 0.5$\mu$ and about 2$\mu$. If the pores are too small, it is believed that the flow rate through the filtration media for desired applications will be too low, or the pressure drop required to generate the desired flow rate will be too high. In addition, if the pore size is too large, it is believed that the polymer covalently bonded to the substrate may not have sufficient density and proximity to sufficiently adsorb microorganisms. A preferred substrate is glass fiber. Preferred glass fiber substrates are available from Ahlstrom Technical Papers. A preferred glass fiber substrate for use in adsorbing virus includes grade 151 glass fiber from Ahlstrom Technical Papers. A preferred glass fiber substrate for the adsorption of bacteria includes grade 164.

In the case of a substrate prepared from particles, it is preferable that the particles are porous and have an average size of between about 5$\mu$ and about 50$\mu$. In general, it is desirable for the particles to have an average pore size of between about 0.2$\mu$ and about 2$\mu$ for the reasons described above in the context of substrates prepared from fibers. In addition, it should be understood that the substrate can be prepared from a mixture of fibers and particles.

The thickness of the substrate is preferably sufficiently small to reduce the incidence of polymer migration to a surface of the substrate in the formation of the filtration media. In general, it is desirable for the polymer to be provided relatively evenly across the entire thickness of the filtration media. It is generally undesirable to have regions in the filtration media which do not include polymer. The absence of polymer in the filtration media reduces the charge density in the filtration media. By providing the filtration media with a relatively thin thickness, it has been found that the polymer can be relatively evenly distributed across the thickness of the filtration media. Furthermore, it is preferable to wrap or layer the filtration media in order to reduce the occurrence of flaws which may be present in a single layer of filtration media. If the manufacture of the filtration media results in a small area not including much polymer, wrapping or layering the filtration media to provide two or more layers reduces the risk of liquid (such as water) passing through the filtration media without being subjected to the attractive forces of the cationic groups on the polymer. In most applications, the filtration media is layered to provide at least two layers, and more preferably between about 2 and about 6 layers. The filtration media can be provided as a pleated media in order to increase the surface area that contacts the liquid. In general, the thickness of the substrate is preferably between about 0.25 mm and about 1.5 mm.

The polymer which is chemically bonded to the substrate is preferably a polymer which does not wash away with the influent, and includes ionic groups that attract microorganisms. In order to enhance the charge density on the substrate, it may be advantageous to provide a mixture of two or more different polymers. Applicants discovered that by mixing different polymers together, it is possible to provide better coverage on the substrate for removal of microorganisms from the liquid. That is, the density of the microorganism attracting groups in the microorganism filtration media can be increased by mixing polymers together and chemically bonding those polymers to the substrate.

The microorganism attracting groups are preferably positively charged groups when provided in a fluid having a pH commonly associated with the pH of drinking water. In general, the pH range of drinking water will be between about 5 and about 9. Exemplary charged groups which have been found to be particularly effective in attracting microorganisms include primary amines, secondary amines, and tertiary amines.

A first polymer which can be used in the polymer composition is a polymer containing cationic charges. The first polymer can include cationic charges on the polymer backbone. A preferred first polymer includes polyamide-polyamine polymer. The polyamide-polyamine polymer having cationic charges on its backbone is preferably a secondary amine based azetidinium polymer having repeating units of the following formula:

I

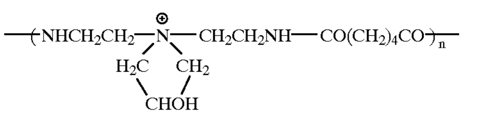

Preferred polyamide-polyamine polymers having repeating units of formula I have an n value of between about 10 and about 100,000, and more preferably between about 1,000 and about 75,000. The polyamide-polyamine polymer preferably has a number average molecular weight of between about 25,000 and 2,000,000 and more preferably between about 500,000 and 1,500,000. The first polymer can be a copolymer including repeating units in addition to those identified as having formula I.

A second polymer which can be used in the polymer composition includes a polymer having cationic charges. The cationic charges can be provided on pendant groups and/or on the backbone. A preferred second polymer Includes a polyamine polymer or a polyamide-polyamine polymer. The polymer having cationic charges on pendant groups Is preferably a tertiary amine based epoxide polymer having repeating units of one or more of the following formula:

II

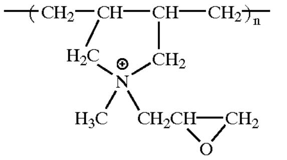

III

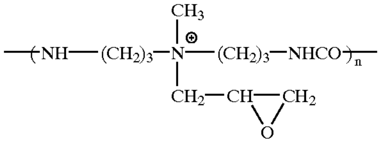

Preferred polymers having repeating units of formulas II and/or III preferably have an n value of between about 10 and about 100,000, and more preferably between about 1,000 and about 75,000. The polymer preferably has a number average molecular weight of between about 25,000 and 2,000,000 and more preferably between about 500,000 and 1,500,000. The second polymer can be a copolymer including repeating units in addition to those identified in formulas II and III. In addition the copolymer can include both of the repeating units in formulas II and III.

A third polymer can be used alone in the polymer composition for forming the filtration media, or in combination with the first polymer and/or the second polymer to provide increased charge density. The third polymer preferably has cationic groups for adsorption of microorganisms. When the third polymer is used in combination with the first polymer and/or the second polymer, it preferably has a sufficiently low molecular weight to allow it to fill the gaps between the first polymer and/or second polymer on the substrate. An advantage to filling gaps between other polymers is increasing the density of charges in the microorganism filtration media. An exemplary polymer which can be used as the third polymer can be prepared from polyethylenimine (PEI). In general, polyethylenimine includes repeating units having the following formula:

$$-\!(CH^2-CH_2-NH)_n\!- \qquad \text{IV}$$

Preferred polyethylenimine polymers have an n value of between about 5 and about 500,000 and, more preferably between about 10 and about 100,000. The polyethylenimine polymer preferably has a number average molecular weight of between about 300 and about 1,000,000. The polyethylenimine polymer can be reacted with a cross-linking agent so that it will react with the substrate and become covalently bonded to the substrate and/or to the other polymers covalently bonded to the substrate. An exemplary crosslinking agent includes bifunctional crosslinking agents such as the diglycidyl ether of 1,4-butanediol. Di-epoxy crosslinking agents are preferred because they provide an epoxy group which can react with an amino group in the polymer, and another epoxy group which can react with the substrate (such as , glass fiber).

In order to provide a third polymer which sufficiently reacts to the substrate surface, it is preferable to react the polyethylenimine polymer with between about 5 wt. % and about 60 wt. % crosslinking agent, and preferably between about 20 wt. % and about 50 wt. %.

The third polymer differs from the first and second polymers in that it is a branched spherical polymer offering a morphology in structure difference and can be reacted with the other polymers. The reaction of the third polymer with the first polymer can be provided, for example, according to the general formula:

V

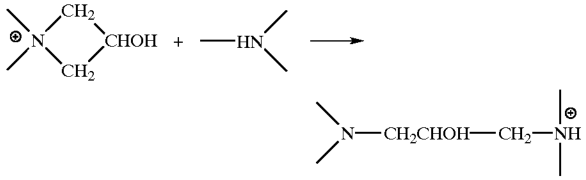

The reaction of the third polymer with other polymers can result in polymer covalently bonded to the substrate and having primary, secondary, and tertiary amines in different ratios for adsorption of microorganisms.

By combining a first polymer having cationic groups with a second polymer having cationic, the charge density in the filtration media can be increased relative to the charge density if only one polymer is covalently bonded to the substrate. In addition, it is expected that the addition of a third polymer further increases the charge density. It is expected that the increased charge density provides a better level of microorganism removal for a given mass of filtration media. It is believed that the charge density of a filtration media corresponds to the number of groups available for microorganism adsorption. The charge density for a microorganism filtration media can be calculated knowing the charge density of the polymer and the weight percent of polymer on the substrate. In general, it is desirable to provide enough polymer on the substrate to provide microorganism adsorption, but not use too much polymer to substantially restrict flow through the filtration media in its intended application. In general, the amount of polymer provided on the substrate is, on a dry basis, between about 0.05 wt. % and about 20 wt. %, and more preferably between about 0.3 wt. % and about 10 wt. %. In general, it is desirable to react a polymer to the substrate which has a high charge density in order to maximize the charge density in the filtration media. Desirable polymers which can be reacted to the substrate include polymers having a charge density of between about 0.1 milliequivalent/gram and about 100 milliequivalent/gram. Preferably, the charge density of the polymer is at least about 1 milliequivalent/gram. The resulting filtration media preferably has a charge density of at least about 0.001 milliequivalent/gram, and preferably in the range of about 0.01 milliequivalent/gram and about 100 milliequivalent/gram. It is expected that the calculated charge density will generally correspond to a charge density determined by titration.

The polymers include reactive groups which allow them to bond to the substrate. Reactive groups which bond to glass include azetidinium and epoxide groups. For example, the following reaction is believed to represent the covalent bonding of a polymer containing azetidinium groups to glass:

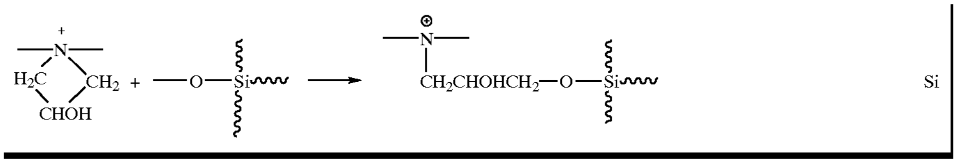

The azetidinium groups can be obtained by reacting a secondary amine with epichlorohydrin.

The following reaction is believed to represent the covalent bonding of a polymer containing epoxy groups to glass:

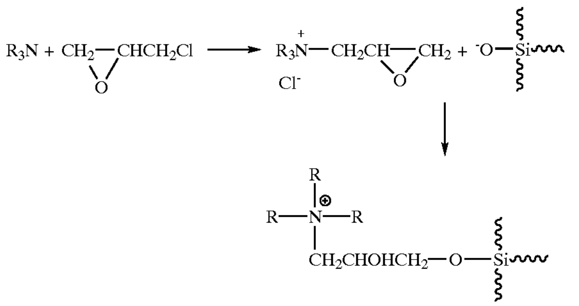

The third polymer can be reacted to the substrate (e.g., glass fiber) as a secondary coating after reaction of the first and/or second polymer to the substrate, or before the reaction of the first and/or second polymer to the substrate. It is expected that the reaction of the third polymer with the first and/or second polymers will result in primary, secondary, tertiary, and quaternary amines in different ratios. By providing for the presence of primary, secondary, tertiary, and quaternary amine groups in the polymer, it is believed that the filtration media will be better able to capture or adsorb microorganisms having different charge characteristics as recorded from their iso-electric point measured by iso-electric focusing method discussed in Murray, Ph.D. Dissertation, Stanford University, 1978.

The proportion of polymers provided in the polymer composition can be varied to provide increased charge density and, therefore, increased adsorptive capacity for the filtration media. Each of the first polymer, the second polymer, and the third polymer can be used alone or in combination with one or more of the other polymers. Preferably, the first polymer and the second polymer are provided at a weight ratio of about 1:9 to about 9: 1, and more preferably at a weight ratio of about 1:2 to about 2:1. When the third polymer is used in combination with the first polymer and the second polymer, it is preferably provided at a weight ratio of first and second polymer to third polymer of between about 9:1 and about 1:9, and more preferably at between about 3:1 and about 1:1. In general, the third polymer is relatively less miscible with the first and second polymers compared with the miscibility of the first and second polymers with each other. Accordingly, when reacting the first, second, and third polymers to the substrate, it is often desirable to react the first and second polymers to the substrate, and then react the third polymer to the substrate.

The polymer composition is preferably reacted to the substrate under conditions which maximize the coverage of the polymer composition on the substrate. It is desirable to provide as much polymer on the substrate as possible in order to increase the charge density of the filtration media. Preferably, the polymer composition is applied to the substrate in an aqueous bath. In general, it is preferable to provide the aqueous bath with a solids content of between about 0.1 wt. % and about 10 wt. %, and more preferably between about 1.0 wt. % and about 7 wt. %. In the situation where the first and second polymers are applied together, followed by application of the third polymer, the first and second polymer can be applied in an aqueous bath containing a weight percent solids of between about 0.1 and about 10, and then the third polymer can be applied in an aqueous bath containing a solids content of between about 0.1 and about 10. In this type of sequential application, it is preferable to react the first and second polymer to the substrate prior to coating the substrate with the third polymer. In addition, the polymers can be applied sequentially in these same solids concentrations.

The substrate is contacted with the polymer bath for a sufficient amount of time to wet the surface of the substrate with the polymer. In general, sufficient wetting usually takes place within about one second to about ten minutes after the substrate is contacted with the polymer bath. Although the polymer can be applied to the substrate by dipping the substrate into an aqueous bath, it should be appreciated that alternative techniques for applying the polymer to the substrate are available. For example, the polymer can be applied as a spray to the substrate. In the case of a spray application, the solids concentrations can be similar to those found in the description of application by aqueous bath. In addition, it should be appreciated that other solids concentrations can be utilized.

Once the polymer is provided on the substrate, the wetted substrate is dried and the polymer is allowed to react with the substrate and with other polymer present on the substrate. Preferably, the wetted substrate is placed in an oven at between about 150° F. and about 400° F. to vaporize the water present and to drive the reaction of the polymer. The polymer-coated substrate is heated in a convective oven at a temperature between about 150° F. and about 400° F. for between about 1 minute and about 30 minutes. If desirable, the polymer-coated substrate can be allowed to drip dry prior to heat treatment.

The pH of the polymer bath can be adjusted to accelerate the reaction. Preferably, the pH is between about 5 and about 11, and more preferably between about 7 and about 9. In the case of glass fibers, the alkalinity serves to activate the glass fibers and additionally acts as a catalyst to accelerate reaction of the polymer on the glass fibers.

The "microorganism removal coefficient" is useful to evaluate the effectiveness of a filter for removing microorganisms from water. The equation and technique for determining the microorganism removal coefficient is described in example 9. In general, microorganism filtration media according to the invention provide a microorganism removal coefficient of at least about 10 ml/g-sec. Preferably, the microorganism filtration media according to the invention provide a microorganism removal coefficient of greater than about 500 ml/g-sec and more preferably greater than about 1,000 ml/g-sec. In particularly preferred applications, the microorganism removal coefficient is about between 100,000 and about 10,000,000 ml/g-sec.

The microorganism filtration media according to the invention can be utilized in many filter applications for providing virus removal from water. Exemplary environments include the filtration of water to provide drinking water. Commercially available devices which are commonly used to filter municipal water can be characterized as faucet mounted filters and pour through filters. Portable filters are additionally available and can be used, according to the invention, for filtering river, stream, and/or lake water to provide drinking water.

Faucet Mounted Filters

Figure 2:
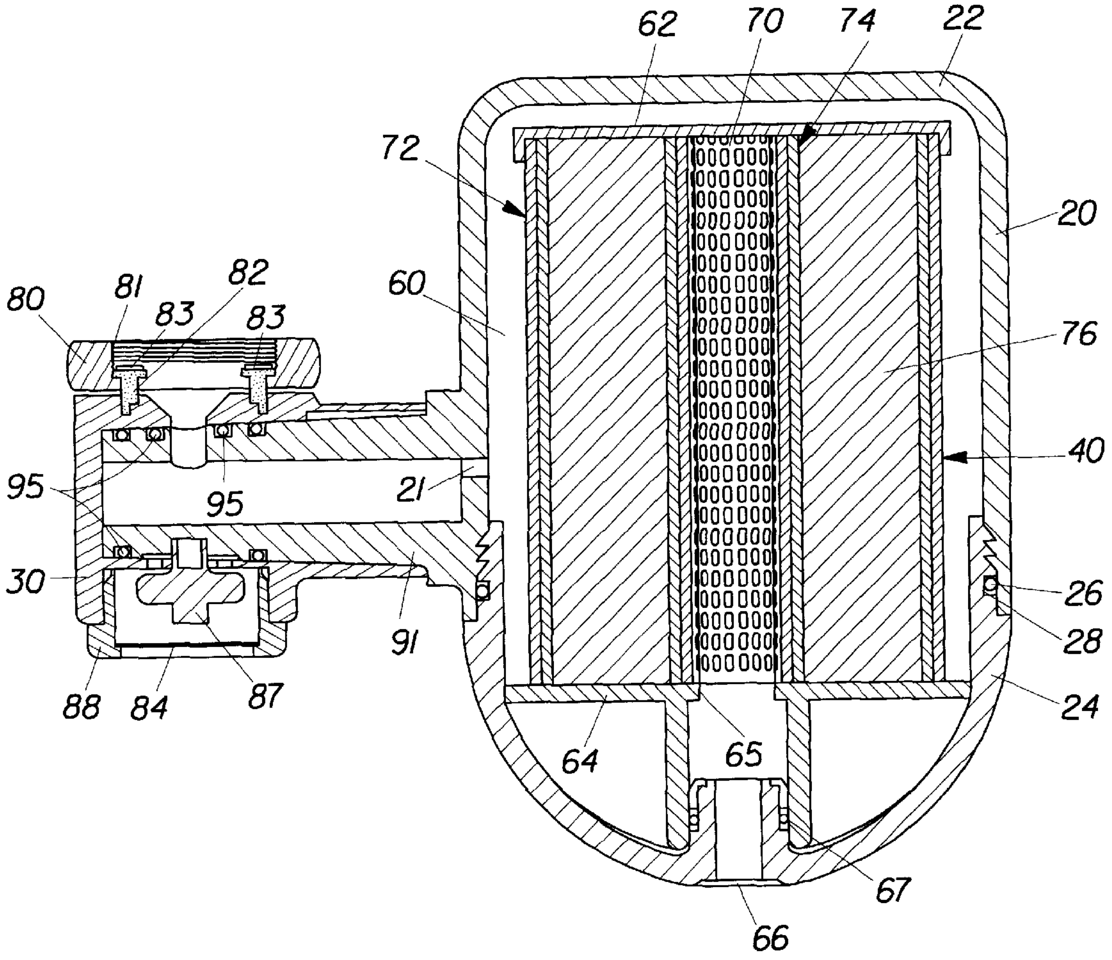
FIG. 2 is a sectional view of the faucet mount filter of FIG. 1 taken along lines 2—2.

Now referring to FIGS. 1 and 2, a faucet mounted filter according to the invention is shown at reference numeral 10. The faucet mounted filter 10 is shown attached to a faucet 12 for treatment of household water.

The faucet mounted filter 10 includes housing 20 which includes upper portion 22 and cap 24 which threads into upper portion 22. A first O-ring 26 is provided in channel 28 to create a water tight seal between upper portion 22 and cap 24. Replaceable filter cartridge 40 is inserted into upper portion 22 from below, and cap 24 is threaded to upper portion 22 to secure cartridge 40 in housing 20.

Water flows through housing 20 and cartridge 40 as follows. Water enters housing 20 from valve body 30 at inlet opening 21, and fills annular space 60 between cartridge 40 and housing 20. Top cap 62 is provided to prevent water from bypassing the cartridge 40. Similarly, a cartridge base 64 is provided to prevent water from bypassing the cartridge 40. The cartridge base 64 includes an opening 65 which allows filtered water to flow out the faucet mounted filter 10 through outlet 66. A second O-ring 67 is provided to seal the cartridge base 64 to the cap 24.

Water flows from the annular space 60 radially through the cartridge 40, and collects inside the support tube 70. The filtered water then flows through the outlet 66. The cartridge 40 includes layers of filtration media 72 and 74 and carbon block 76. The layers of filtration media 72 and the layers of filtration media 74 are shown as a wrap of two layers of filtration media. It should be appreciated that the filtration media can include one layer or several layers of filtration media. In addition, the cartridge 40 can be provided with filtration media 72 but without filtration media 74, and vice versa. Support tube 70 is provided to hold the filtration media 72 relative to the carbon block 76. The support to 70 is preferably a porous tube which does not substantially restrict the flow of water therethrough, but supports the filtration media 74. In general, the filtration media 72 and 74 and the carbon block 76 are preferably adhered together at the bottom and the top of the cartridge and to the top cap 62 and the cartridge base 64 with adhesive.

Although the cartridge 40 is shown with a carbon block 76, it should be understood that the carbon block can be replaced with another type of filter if the carbon block is not desired for a particular application. For example, it may be advantageous to replace the carbon block 76 with a pleated filtration media according to the invention.

The flow of water through the cartridge 40 can be diverted by rotating the housing 20 along the direction of the arrow shown in FIG. 1. The valve body 30 attaches to the faucet 12 via threaded mounting member or nut 80 having threads 81. A retainer ring 82 is attached to valve body 30 so that the mounting member 80 is free to rotate. A washer 83 seals the retainer ring 82 to the end of the faucet 12. The body retainer 87 holds the valve body onto the stem 91, and allows rotation of the housing relative to the valve body 30 along the direction of the arrow in FIG. 1. By rotating the housing 20, the flow of water can be diverted to the filter or alternatively to the aerator 88 and outlet 84. Additional O-rings 95 are provided to reduce leakage.

Figure 3:
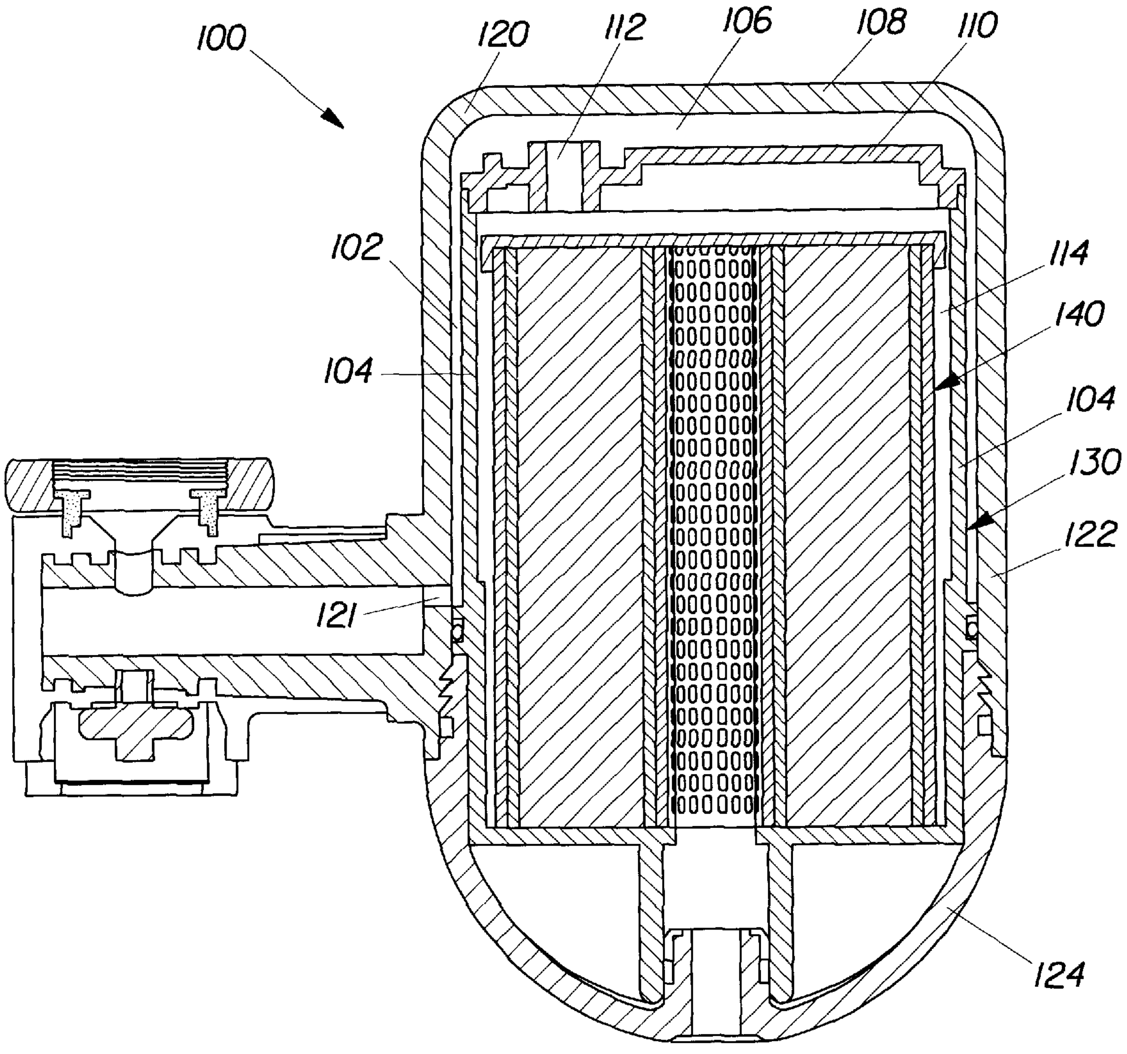
FIG. 3 is a sectional view of an alternative embodiment of faucet mount filter according to the principles of the invention.

Now referring to FIG. 3, an alternative embodiment of the faucet mounted filter is shown at reference numeral 100. The faucet mounted filter 100 includes many of the features identified in the faucet mounted filter 10. Water flows through the inlet opening 121 and into the annular space 102 between the housing 120 and the inner housing 104. The water then flows into the top channel 106 provided between the housing top 108 and the inner housing top 110. The water then flows through the passage 112 and into the inner annular channel 114 provided between the cartridge 140 and the inner housing 104. The flow of the water through the cartridge 140 is similar to that described above with respect to FIG. 2.

An advantage of the arrangement shown in FIG. 3 is that the filter cartridge 140 and inner housing 104 serve to provide a more convenient replacement filter 130. Accordingly, the replacement filter 130 can easily be removed from the faucet mounted filter 100 by detaching the cap 124 from the upper portion 122, removing the used filter and introducing a new filter, and screwing the cap 124 to the upper portion 122. An advantage is that a single O-ring 126 can be provided in the housing 120 between the filter 130 and the upper portion 122.

A faucet mounted filter which can be modified to include the filtration media of the invention includes the faucet mounted filter described in U.S. Pat. No. 5,525,241, the disclosure of which is incorporated herein by reference in its entirety.

Pour Through Filters

Figure 4:
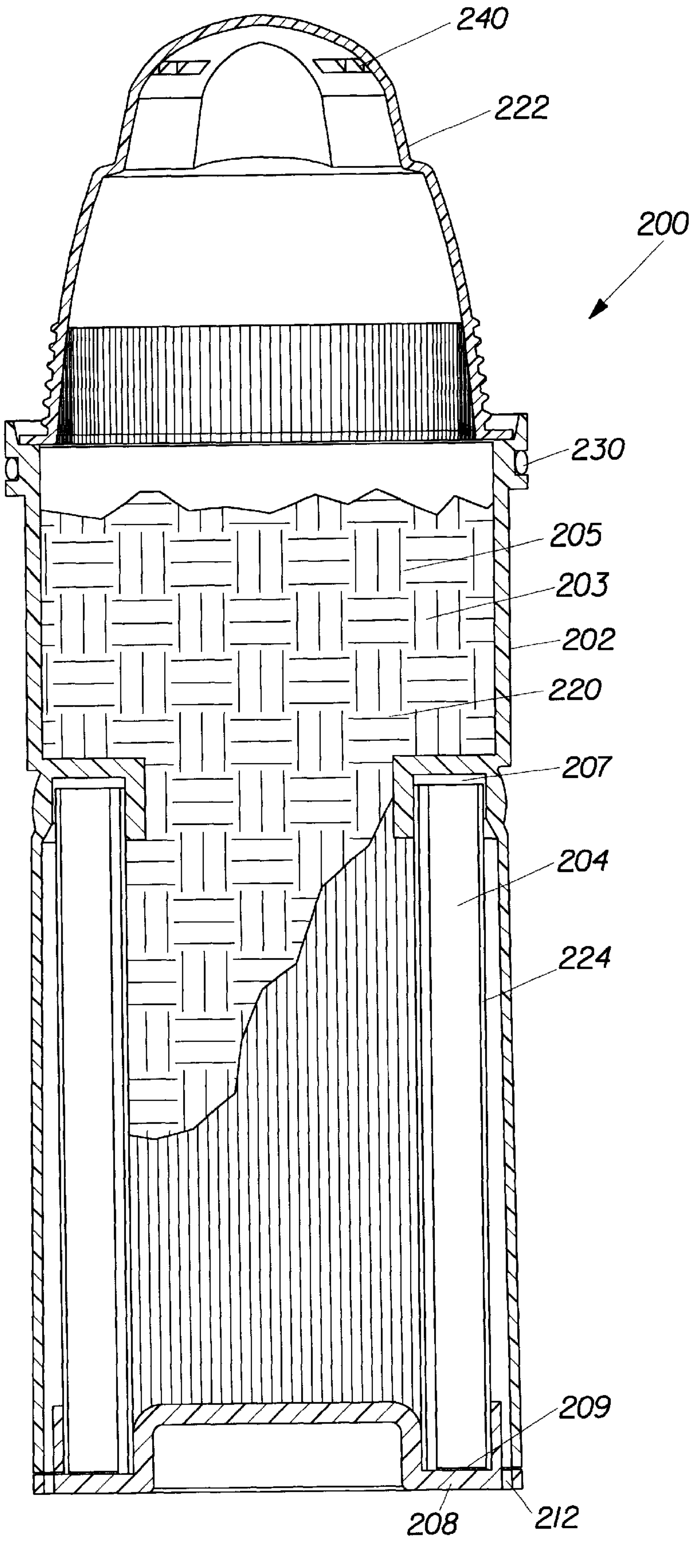
FIG. 4 is a sectional view of a pour through filter according to the principles of the invention.

Now referring to FIG. 4, a pour through filter cartridge is shown at reference numeral 200. The pour through filter cartridge 200 can be placed in a conventional carafe type filtration reservoir. These types of filtration reservoirs are available commercially from Recovery Engineering, Inc. and Britia.

The pour through filter cartridge 200 includes an outer shell 202 and an interior region 203 which includes a filter 205. The filter 205 includes a pleated filtration media 204 which is glued to the outer shell 202 with hot melt adhesive 206. A bottom cap 208 is glued to the bottom of the filtration media 204 by hot melt adhesive 209. Openings 212 are provided to allow water to exit the pour through filter cartridge 200.

Loose media 220, such as granular carbon and/or ion exchange resin, can be placed in the inside the interior region 203 as part of the cartridge 200. A slotted cover 222 can be fastened to the top of the outer shell 202 to contain the loose media. To add redundancy, a separate cylinder of filtration media 224 can be wrapped outside of the pleated media 204.

A seal 230 is provided to prevent water from bypassing the cartridge 200. Accordingly, water provided in the upper region of a conventional carafe type filtration reservoir will flow through the opening 240 and into the interior region 203 of the cartridge 200. The water then flows through the filter 205 which includes the loose media 220 and outward through the filtration media 204 and 224 (if present) and exits through openings 212.

The pleated filtration media 204 and the wrapped filtration media 224 are preferably provided from the polymer treated filtration media according to the invention.

The entire disclosure of U.S. patent application Ser. No. 08/843,358, filed Apr. 16, 1997, is incorporated herein by reference. The filtration media of the invention can be provided in the filter described in U.S. patent application Ser. No. 08/843,358.

Experimental

Figure 5:
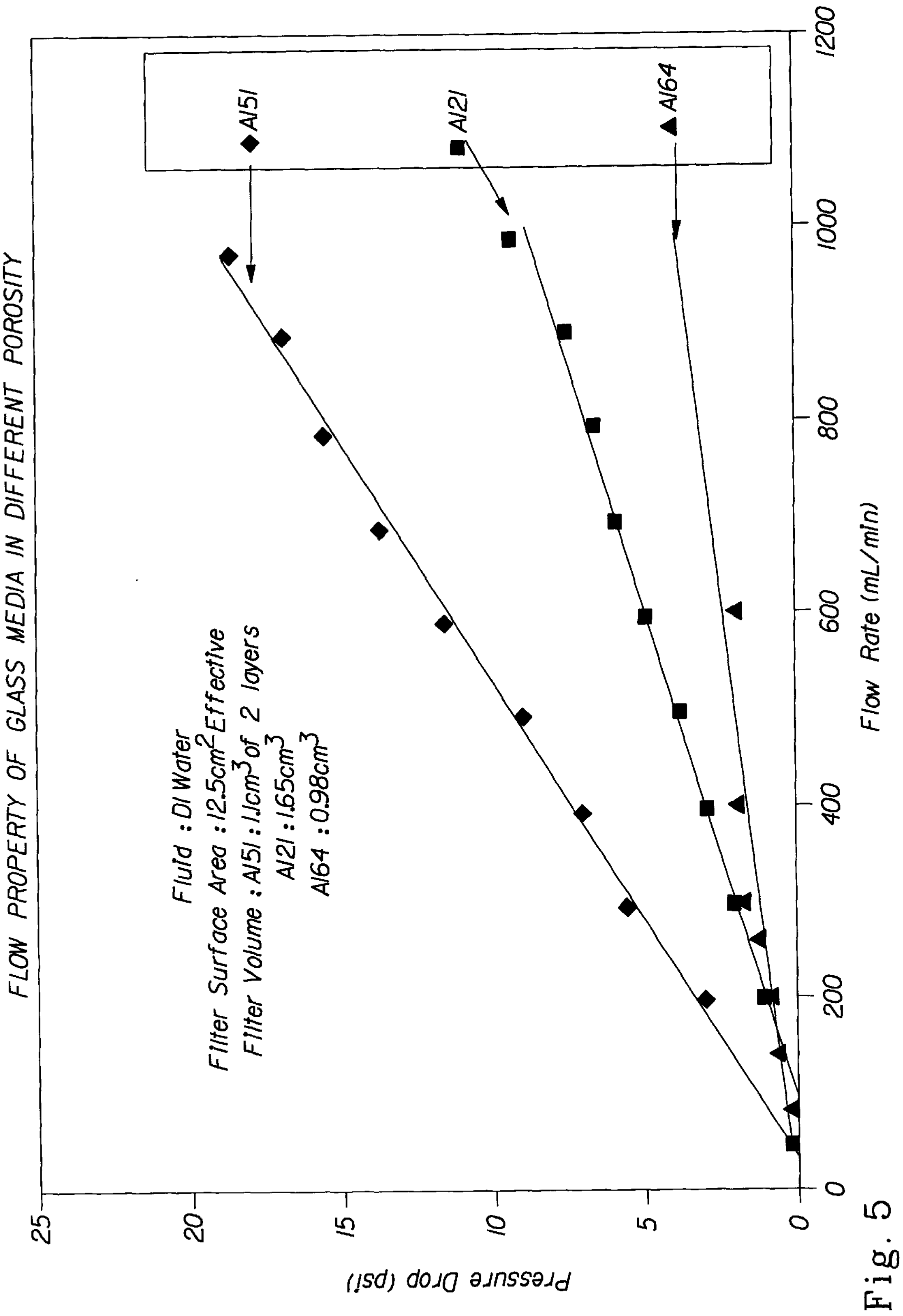
FIG. 5 is a graph of flow properties for glass media.

Preparation of Filtration Media:

Glass fiber filter media of different porosity used in this study are characterized by measuring the flow rate vs. pressure across the filter as shown in FIG. 5. The pore size in such media are non-uniform and can not be precisely defined. Grade 151 filter from Ahlstrom Technical Papers does show certain amount of bacteria reduction. This is believed due to the mechanical screening. The results with grade 164 support this contention. See example 8.

Preparation of Polymeric Coating Solution:

Polymer A is a secondary amino based azetidinum type polymer. This polymer has a secondary amine inserted in polymeric amide groups and will be further reacted with epichlorohydrin to form azetidium groups for cross-linking to hydroxyl or amino groups as disclosed in U.S. Pat. Nos. 2,926,154 and 2,926,116.

Polymer B is a tertiary amine based epoxide type polymer formed by radical initiated polymerization of alkyl dialkyamine typically methyl dialkyl amine (MDAA). The tertiary amine can react with epichlorohydrin to form glycidyl quaternary ammonium polymers, that can be stabilized as their chlorohydrin form. They have been characterized as alkaline curing wet strength resins. See U.S. Pat. Nos. 3,700,633, 3,772,076, 3,833,531.

Figure 6:
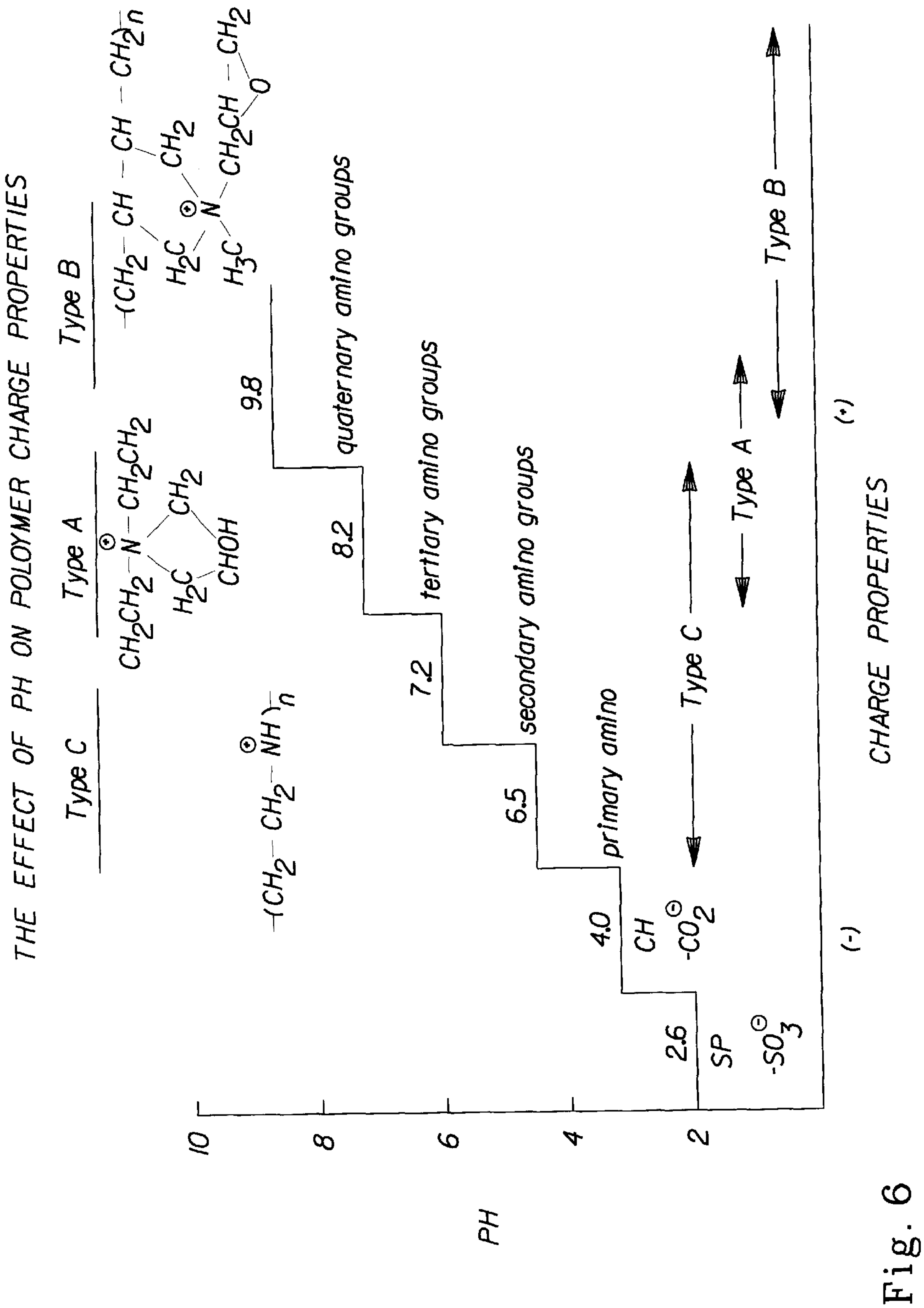
FIG. 6 is a graph representing the effect of pH on polymer charge properties.

The above two polymers are compatible and can be mixed in different proportions and diluted to the required concentration with water, then alkaline adjusted to pH about 9.0 for dip coating the glass fiber media. Cross-linking reaction will start as soon as water molecules are removed from the media during drying. The polymeric coating in this case is the mixture of secondary, tertiary and quaternary in different proportion with their charge strength in pH range shown in FIG. 6.

Both polymers A and B provide a charge density of about 3.0 milliequivalence/gram. However, we found it is the molecular structure differences and the location of charge sites maximizes their interaction toward microorganisms. The polymer reacted to the glass fiber should be provided in an amount which does not substantially interfere with the flow properties of the filtration media, but which provides a desired level of microorganism adsorption. In addition, it is desirable that the polymer is covalently bonded to the substrate so that polymer remains with the substrate and does not leech into the water or liquid which is being filtered. In general, it is desirable to provide enough polymer on the substrate to provide microorganism adsorption, but not use too much polymer to substantially restrict flow through the filtration media in its intended application.

Assay Technique:

MS-2 has no membranes and behaves very much like a small protein-DNA complex molecule, thus are quite stable in water over a wide range of temperatures.

MS-2 are assayed according to the procedure by Hurst, C., "Appl. Environ. Microbiol. 60:3462 (1994). The bacteriophages and corresponding bacterial host strains used in this study were as follows: MS-2 (ATCC 15597-BI) and its host *Escherichia Coli* C-3000 (ATCC 15597) were purchased from American Type Culture Collection, Rockville, Md. The basic medium used for propagation of host bacteria were modified LB medium (medium 1065 ATCC). Bacteriophage plaque formation assays were performed in 10-cm diameter petri plates, using the traditional double layer agar technique. The bottom agar layer consisted of LB medium containing 1% agar (Bacto agar, Difco). The top agar layer was based on LB medium containing 0.8% agar. The top agar layer of each plate consisted of 3 ml of top agar medium; 1 ml of MS2 diluted in LB medium; and 0.2 m. of a fresh culture of bacterial host in LB medium. Inoculation of the assay plates to allow plaque formation was performed for 16 hours 37° C. Viral titers were calculated as PFU (plaque forming unit) per ml of the diluted bacteriophage.

The *E-Coli* grown in proper conditions will have receptors that strongly attract MS-2 to form plaques. High accuracy can only be achieved in the proper ratio of the right amount of MS-2 to *E-Coli.*

EXAMPLE 1

Effect of Virus Adsorption with Change in Virus Concentration and Polymer Coating Influent water containing bacteriophage MS-2 virus of 28 nm at concentrations of $2\times10^9$, $8\times10^7$, and $2\times10^6$ PFU/ml were passed through two layers of filtration media. The layers of filtration media can be characterized as type A filtration media (A), type B filtration media (B), mixed type A and B filtration media (AB), and sequentially applied type A and B filtration media (A then B). The mixed type A and B filtration media can be prepared by reacting a mixture of polymers A and B onto the filtration media to provide the AB filtration media. By reacting the A polymer onto the reaction media and then reacting the B polymer onto the reaction media, the A then B filtration media is produced.

Type A filtration media was prepared by providing a web of glass fiber (grade 151 from Ahlstrom Technical Papers) and reacting a secondary amine based azetidinium polymer to the web of glass fiber. The secondary amine based azetidinium polymer has the following formula:

I

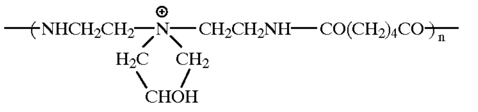

The secondary amine based azetidinium polymer has a number average molecular weight of about 1,000,000 and is available in water at solid weight percent of 30% and a pH of between four and five. This polymer is referred to herein as the A polymer.

The type B filtration media was prepared by reacting a tertiary amine based epoxide polymer to the web of glass fiber. The glass fiber used was grade 151 glass fiber from Ahlstrom Technical Papers. The tertiary amine based epoxide polymer has the following structure:

II

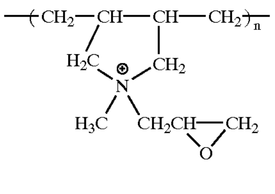

The tertiary amine based epoxide has a number average molecular weight of about 1,000,000, and is available in water having a solid weight percent of about 20% and a pH of between four and five. This polymer is referred to herein as the B polymer.

The AB filtration media was prepared by reacting a mixture of A polymer and B polymer to a web of grade 151 glass fiber from Ahlstrom Technical Papers.

The A then B filtration media was prepared by reacting polymer A to a web of grade 151 glass fiber available from Ahlstrom Technical Papers. Once the polymer A has reacted to the glass fiber, polymer B is then reacted to the glass fiber.

The filtration media identified in Table 1 refers to the weight percent of polymer provided in the polymer bath that was used to prepare the filtration media. The filtration media was prepared by providing a polymer bath having the indicated weight percent of polymer A and/or B identified in Table 1 as a solids weight percent. The glass fiber was then immersed in the polymer bath. Once the glass fiber was determined to be fully wetted, it was removed and allowed to drip dry for approximately five minutes, and then placed in a convective oven at 300° F. for approximately six minutes. The weight percent solids was altered for the samples. The weight percent solids in the polymer bath is reported in the second column of Table 1. For example, the filtration media of sample number 1 was prepared from a bath including 1.5 wt. % polymer A, and sample number 2 was prepared from a polymer bath including 3.0 wt. % polymer A. In the case where the polymer bath includes a mixture of polymer A and polymer B, the ratio of polymer A to polymer B is 1:1 on a weight basis.

The flow rate of bacteriophage MS-2 virus through the filtration media was controlled at 200 ml/min. The filtration media was cut to a 47 millimeter disc and placed in a 47 millimeter membrane filter holder. The pressure drop across the filter is less than 5 psi, and the effective filter surface area is approximately 12.5 $cm^2$. The estimated contact time is about 0.1 seconds assuming 50% media porosity. The pH of the influent was maintained at about 9.

The results of this example are reported in Table 1. The column entitled "Wt. Gain %" refers to the weight of polymer added to the glass fiber. The influent concentration is reported in Table 1.

The favorable adsorption kinetics on virus by such filter media are shown by this example. Sample numbers 1–4 show that the polymer concentration effect plateaus off at about the 6% level, and preferably at the 3% level. The type B filtration media is slightly better on capturing the virus than the type A filtration media. The best result can be seen in sample number 6 of 1:1 weight ratio mixture of polymers A and B. The double coating process by coating a second layer of type B resin after type A prove to be advantageous as shown in sample number 5.

The data demonstrates a relationship between charge density, virus concentration, and contact time requirement. The filtration media is relatively effective in removing virus of lower concentration around $10^6$ PFU/ml by even a single polymer coating whereas a mixed polymer coating or longer contact time is advantageous for the removal of $10^9$ PFU/ml virus to achieve results of higher than 4 log reduction.

TABLE 1

The effect of virus concentration on removal by chemical adsorption.

| | | | High | | Med | | Low | |
|---|---|---|---|---|---|---|---|---|
| | | | Influent Conc. (PFU/ml) | | | | | |
| | Solids | | $2.0 \times 10^9$ | | $8.0 \times 10^7$ | | $2.0 \times 10^6$ | |
| Sample Number | Concentration and Polymer | Wt. Gain % | Effluent (PFU/ml) | Log Red'n | Effluent (PFU/ml) | Log Red'n | Effluent (PFU/ml) | Log Red'n |
| 1 | 1.5% A | 8.4 | $6.8 \times 10^8$ | 0.5 | $6.4 \times 10^5$ | 2.1 | 50 | 4.6 |
| 2 | 3.0% A | 17 | $7.0 \times 10^8$ | 0.5 | $3.0 \times 10^5$ | 2.4 | 80 | 4.4 |
| 3 | 1.5% B | 8 | $6.6 \times 10^8$ | 0.5 | $2.8 \times 10^5$ | 2.5 | 50 | 4.6 |
| 4 | 3.0% B | 16 | $6.0 \times 10^8$ | 0.5 | $1.5 \times 10^5$ | 2.7 | 30 | 4.8 |
| 5 | 1.5% A then 1.5% B | 15 | $5.0 \times 10^8$ | 0.6 | $1.0 \times 10^2$ | 5.9 | <10 | >5.3 |
| 6 | 1.5% AB Mix | 20.3 | $1.0 \times 10^3$ | 6.3 | <10 | >6.9 | <10 | >5.3 |
| 7 | 3% AB Mix | 27.5 | $4.0 \times 10^6$ | 2.7 | 60 | 6.2 | <10 | >5.3 |
| 8 | .75% A then .75% B | 8.33 | $9.6 \times 10^8$ | 0.3 | $2.0 \times 10^5$ | 2.6 | <10 | >5.3 |
| 9 | 6% B | 41 | $4.0 \times 10^6$ | 2.7 | — | — | 100 | 4.3 |
| 10 | None-Control | — | — | — | $4.0 \times 10^7$ | .3 | — | — |

EXAMPLE 2

Effect of Third Polymer on MS-2 Adsorption

The adsorptive properties of filtration media including a third polymer (polymer C) was compared to that of filtration media including polymer A and filtration media including polymers A and B. Polymer C was prepared from a polyethylenimine (PEI) polymer have the following structure:

$$-(CH_2-CH_2-NH)_n- \qquad \text{IV}$$

The polyethylenimine polymer was provided having a number average molecular weight of 800 and in a water solution at a solids weight percent of 98%. One part PEI polymer was emulsified (under strong mechanical agitation) with 0.5 part diglycidyl ether of 1,4-butanediol and allowed to form a colloidal solution. The polymer was then diluted to 1 wt. % solids to provide polymer C. Polymer C was applied to glass fiber according to the technique described in Example 1. The filtration media identified by sample numbers 9 and 10 in Table 2 were prepared by reacting polymer C onto AB filtration media. The polymer concentration used to form the filtration media are identified in Table 2. It should be understood that for sample numbers 9 and 10, polymers A and B were reacted to the glass fiber, then polymer C was reacted.

The procedure of Example 1 was repeated for the samples identified in Table 2. The flow rate of filtrate was provided at 200 ml/min through two layers of filtration media. The contact time was approximately 0.165 seconds and the volume filtered was 500 ml. The results are reported in Table 2.

Sample numbers 9 and 10 demonstrate the additional contribution of using a third polymers as a second coating. It is believed that polymer C patches the gaps between the polymers A and B).

TABLE 2

The effect of virus concentration on removal by chemical adsorption.

| Sample | Solids Concentration and | MS-2 (PFU/ml) | | Log |
|---|---|---|---|---|
| Number | Polymer | In | Out | Reduction |
| 1 | no | $2 \times 10^8$ | $1.3 \times 10^8$ | 0.2 |
| 2 | 0.75% A | $8 \times 10^7$ | $2 \times 10^6$ | 1.6 |
| 3 | 1.50% A | $2 \times 10^8$ | $6.4 \times 10^6$ | 1.5 |
| 4 | 3.0% A | $8 \times 10^7$ | $8.5 \times 10^5$ | 1.9 |
| 5 | 1.5% A | $2 \times 10^8$ | $1.4 \times 10^7$ | 1.2 |
| 6 | 1.5% AB | $2 \times 10^8$ | $5 \times 10^1$ | 7.4 |
| 7 | 1.5%AB | $8 \times 10^7$ | $1 \times 10^2$ | 5.9 |
| 8 | 3.0% AB | $8 \times 10^7$ | $2 \times 10^1$ | 6.6 |
| 9 | 1.5% AB + 1.0% C | $2 \times 10^8$ | <10 | <7.3 |
| 10 | 3.0% AB + 1.0% C | $8 \times 10^7$ | <10 | <6.9 |
| 11 | 3.0% AB | $2 \times 10^8$ | $2 \times 10^2$ | 6.0 |
| 12 | 3.0% AB | $8 \times 10^7$ | $12 \times 10^2$ | 4.8 |

EXAMPLE 3

Effect of Polymer Concentration and Adsorption Time on MS-2 Removal

This example illustrates the relationship between the adsorption time and the virus removal efficiency. The amount of filtration media and the flow rate are factors affecting the virus adsorption time. The efficiency of virus adsorption increases with increasing adsorption time by either reducing the flow rate or increasing the amount of filtration media.

The general procedures identified in the above examples were followed while varying the contact time. It should be understood that the contact time is the time the filtrate is in contact with the filtration media. Accordingly, the thickness or number of layers of filtration media and the flow rate were varied to alter contact time. The results are reported in Table 3.

The most preferred results were obtained by preparing the filtration media from an aqueous polymer bath containing 2.5 to 3% by weight of a 1:1 weight ratio of polymers A and B. As shown in Table 3, sample numbers 6–10 achieve greater than a 6.9 log reduction of MS-2.

Measurements were obtained for each sample after one liter of water flowed through the filtration media at the indicated flow rate. The same filtration media was tested at increasing flow rates. For example, sample numbers 1 and 2 are the results of testing conducted on one filtration media. Sample numbers 3–5 were the result of test conducted on another filtration media.

TABLE 3

Effect of Contact Time on MS-2 Adsorption

| Sample Number | Solids Concentration and Polymer | No. of Layers | Flow Rate (ml/min) | Contact Time (sec) | MS-2 (PFU/ml) In | MS-2 (PFU/ml) Out | Log Reduction |
|---|---|---|---|---|---|---|---|
| 1 | 1.5% AB | 2.0 | 500 | 0.066 | $2 \times 10^8$ | $2.5 \times 10^6$ | 1.9 |
| 2 | 1.5% AB | 2.0 | 1,000 | 0.033 | $2 \times 10^8$ | $1.0 \times 10^7$ | 1.3 |
| 3 | 1.5% AB | 3.0 | 500 | 0.099 | $2 \times 10^8$ | $2.0 \times 10^4$ | 4.0 |
| 4 | 1.5% AB | 3.0 | 1,000 | 0.049 | $2 \times 10^8$ | $1.0 \times 10^5$ | 3.3 |
| 5 | 1.5% AB | 3.0 | 1,500 | 0.033 | $2 \times 10^8$ | $9.0 \times 10^7$ | 0.35 |
| 6 | 2.5% AB | 2.0 | 200 | 0.165 | $8 \times 10^7$ | <10 | >7.0 |
| 7 | 2.5% AB | 2.0 | 500 | 0.066 | $8 \times 10^7$ | <10 | >7.0 |
| 8 | 2.5% AB | 2.0 | 1,000 | 0.033 | $8 \times 10^7$ | <10 | >7.0 |
| 9 | 3.0% AB | 2.0 | 500 | 0.066 | $8 \times 10^7$ | <10 | >7.0 |
| 10 | 3.0% AB | 2.0 | 1,000 | 0.033 | $8 \times 10^7$ | <10 | >7.0 |

$$\text{Contact Time} = \frac{\text{Surface Area} \times \text{Media Thickness} \times \text{Median Porosity}}{\text{Flow Rate}}$$

$$= \frac{12.5\ \text{cm}^2 \times 0.044\ \text{cm} \times \text{no. of layers}}{\text{Flow Rate}}$$

EXAMPLE 4

Effect of AB Concentration on MS-2 Removal

This example illustrates the viral removal capability as a function of charge density of AB mixture on filtration media. The filtration media was prepared according to the general technique described in Example 1. The polymer bath was prepared from polymer A and polymer B provided at a 1:1 wt. ratio at the weight percent solids identified in Table 4 for each of the samples. The glass fiber used was grade 151 glass fiber from Ahlstrom Technical Papers. The filtration media tested has a surface area of 12.5 $cm^2$ and thickness of 0.044 cm. The flow rate was 500 ml/min and the contact time was 0.033 seconds. The results of this example are reported in Table 4.

Virus breakthrough point is the level at which virus adsorption onto the filtration media no longer occurs at desirable levels. That is, it is believed that the sites for binding the virus have become tied up or saturated, and the virus begins flowing through the filtration media rather than being adsorbed onto the filtration media.

It is believed that the mixture of polymers A and B delay the virus breakthrough point for the tested filtration media. In addition, increase in concentration of polymers A and B on the filtration media tend to delay virus breakthrough point.

In Table 4 and many of the subsequent tables in this application, it should be appreciated that many of the reported samples are actually part of the same test measurement. For example, in Table 4, sample numbers 1–6 were obtained from a test of a particular filtration media. Measurements were obtained after a given volume of effluent flowed through the filtration media.

TABLE 4

Effect of AB Concentration on MS-2 Adsorption

| Sample Number | Solids Concentration and Polymer | No. of Layers | Volume Filtered (ml) | MS-2 (PFU/ml) In | MS-2 (PFU/ml) Out | Log Reduction |
|---|---|---|---|---|---|---|
| 1 | 1.5% AB | 1.0 | 500 | $1.8 \times 10^6$ | <10 | >5.25 |
| 2 | 1.5% AB | 1.0 | 1,000 | $1.8 \times 10^6$ | $1 \times 10^1$ | 5.25 |
| 3 | 1.5% AB | 1.0 | 2,000 | $1.8 \times 10^6$ | $6 \times 10^2$ | 3.48 |
| 4 | 1.5% AB | 1.0 | 3,000 | $1.8 \times 10^6$ | $4 \times 10^4$ | 1.66 |
| 5 | 1.5% AB | 1.0 | 4,000 | $1.8 \times 10^6$ | $2 \times 10^5$ | 0.95 |
| 6 | 1.5% AB | 1.0 | 5,000 | $1.8 \times 10^6$ | $3 \times 10^5$ | 0.78 |
| 7 | 2.0% AB | 1.0 | 1,000 | $1.8 \times 10^6$ | <10 | >5.25 |
| 8 | 2.0% AB | 1.0 | 2,000 | $1.8 \times 10^6$ | $17 \times 10^2$ | 3.02 |
| 9 | 2.0% AB | 1.0 | 3,000 | $1.8 \times 10^6$ | $26 \times 10^3$ | 1.84 |
| 10 | 2.0% AB | 1.0 | 4,000 | $1.8 \times 10^6$ | $6 \times 10^4$ | 1.48 |
| 11 | 2.0% AB | 1.0 | 5,000 | $1.8 \times 10^6$ | $2 \times 10^5$ | 0.95 |
| 12 | 2.5% AB | 1.0 | 1,000 | $1.8 \times 10^6$ | <10 | >5.25 |
| 13 | 2.5% AB | 1.0 | 2,000 | $1.8 \times 10^6$ | $17 \times 10^1$ | 4.02 |
| 14 | 2.5% AB | 1.0 | 3,000 | $1.8 \times 10^6$ | $3 \times 10^3$ | 2.78 |
| 15 | 2.5% AB | 1.0 | 4,000 | $1.8 \times 10^6$ | $3 \times 10^4$ | 1.78 |
| 16 | 2.5% AB | 1.0 | 5,000 | $1.8 \times 10^6$ | $4 \times 10^4$ | 1.65 |
| 17 | 3.0% AB | 1.0 | 1,000 | $4 \times 10^6$ | <10 | >5.6 |
| 18 | 3.0% AB | 1.0 | 2,000 | $4 \times 10^6$ | <10 | >5.6 |

TABLE 4-continued

Effect of AB Concentration on MS-2 Adsorption

| Sample Number | Solids Concentration and Polymer | No. of Layers | Volume Filtered (ml) | MS-2 (PFU/ml) In | MS-2 (PFU/ml) Out | Log Reduction |
|---|---|---|---|---|---|---|
| 19 | 3.0% AB | 1.0 | 3,000 | $4 \times 10^6$ | <10 | >5.6 |
| 20 | 3.0% AB | 1.0 | 4,000 | $4 \times 10^6$ | $2 \times 10^1$ | 5.3 |
| 21 | 3.0% AB | 1.0 | 5,000 | $4 \times 10^6$ | $1 \times 10^2$ | 4.6 |
| 22 | 3.0% AB | 1.0 | 6,000 | $4 \times 10^6$ | $1 \times 10^3$ | 3.6 |

EXAMPLE 5

Effect of Virus Concentration on Filter Breakthrough Point

This example demonstrates the effect of virus concentration on filter breaktrough point. It should be appreciated that the breakthrough point refers to the point where the filter starts to show the failure on capturing the organism. It differs from the previous Example 4 in that the capacity may not be fully utilized yet the efficiency on capturing the microorganism decreases due to loss in number of active sites.

The samples were prepared according to Example 1. One layer of filtration media was subjected to a flow rate of 200 ml/min which resulted in a contact time of 0.082 seconds. The filtration media tested was prepared from grade 151 glass fiber available from Ahlstrom Technical Papers, and a bath containing 1.5 wt. % A polymer and B mixed polymer wherein A polymer and B polymer were mixed at 50/50 ratio then reacted to 151 glass fiber. The results show that no breakthrough occurred at low virus concentration of $1 \times 10^4$ PFU/ml under the specified test conditions, whereas virus at $1 \times 10^5$ PFU/ml breaks after 400 ml filtered and $1 \times 10^6$ PFU/ml breaks early indicating that the high number of MS-2 quickly saturates the available capturing sites resulting in early breakthrough.

TABLE 5

The Effect of Virus Concentration on Filter Breakthrough Point

| Sample Number | Volume Filtered (ml) | MS-2 (PFU/ml) In | MS-2 (PFU/ml) Out | Log Reduction |
|---|---|---|---|---|
| 1 | 50 | $1 \times 10^6$ | <10 | >5.0 |
| 2 | 150 | $1 \times 10^6$ | $1 \times 10^2$ | 4.0 |
| 3 | 200 | $1 \times 10^6$ | $1 \times 10^3$ | 2.3 |
| 4 | 300 | $1 \times 10^6$ | $3 \times 10^5$ | 0.6 |
| 5 | 400 | $1 \times 10^6$ | $5 \times 10^5$ | 0.3 |
| 6 | 500 | $1 \times 10^6$ | $5 \times 10^5$ | 0.3 |
| 7 | 50 | $1 \times 10^5$ | <10 | >4.0 |
| 8 | 100 | $1 \times 10^5$ | <10 | >4.9 |
| 9 | 200 | $1 \times 10^5$ | <10 | >4.0 |
| 10 | 300 | $1 \times 10^5$ | $1 \times 10^1$ | 4.0 |
| 11 | 400 | $1 \times 10^5$ | $1 \times 10^2$ | 3.0 |
| 12 | 500 | $1 \times 10^5$ | $4 \times 10^2$ | 2.4 |
| 13 | 50 | $1 \times 10^4$ | <10 | >3.0 |
| 14 | 100 | $1 \times 10^4$ | <10 | >3.0 |
| 15 | 200 | $1 \times 10^4$ | <10 | >3.0 |
| 16 | 300 | $1 \times 10^4$ | <10 | >3.0 |
| 17 | 400 | $1 \times 10^4$ | <10 | >3.0 |
| 18 | 500 | $1 \times 10^4$ | <10 | >3.0 |

Example 6

Effect of Filter Porosity

This example is provided to show the effect of filter porosity on virus absorption. In this example, glass filter media having grade 164 and 151 from Ahlstrom Technical Papers were compared. The filtration media was prepared according to the technique described in Example 1 where the polymer bath includes 1.5 wt. % of polymer A and polymer B provided at a weight ratio of 1:1. The filtration media was provided as a single layer having a thickness of 0.04 mm and a surface area of 12.5 $cm^2$. The flow rate through the filtration media was 500 ml/min and the contact time was 0.033 seconds. Sample numbers 1–8 were prepared from glass fibers having grade 164. Sample numbers 9–15 were prepared using glass fibers having grade 151. The results of this example are reported in Table 6.

Media grade 164 being relatively larger in pore size than that of 151 was found to be less effective on MS-2 adsorption under identical testing conditions. It is believed that the reduced effectiveness in microorganism capturing by filters of relatively larger pores can be compensated by providing a thicker media (i.e., more layers) or by cross-linking with more charged groups to improve the contact efficiency between the microorganism and their adsorptive groups on the filtration media.

TABLE 6

The Effect of Filter Porosity on MS-2 Adsorption

| Sample Number | Solids Concentration and Polymer | Volume Filtered (ml) | MS-2 (PFU/ml) In | MS-2 (PFU/ml) Out | Log Reduction |
|---|---|---|---|---|---|
| 1 | 1.5% AB | 500 | $3 \times 10^6$ | $6 \times 10^3$ | 2.67 |
| 2 | 1.5% AB | 1,000 | $3 \times 10^6$ | $3 \times 10^4$ | 2.00 |
| 3 | 1.5% AB | 1,500 | $3 \times 10^6$ | $13 \times 10^4$ | 1.37 |
| 4 | 1.5% AB | 2,000 | $3 \times 10^6$ | $19 \times 10^4$ | 1.10 |
| 5 | 1.5% AB | 2,500 | $3 \times 10^6$ | $6 \times 10^5$ | 0.67 |
| 6 | 1.5% AB | 3,000 | $3 \times 10^6$ | $7 \times 10^5$ | 0.64 |
| 7 | 1.5% AB | 3,500 | $3 \times 10^6$ | $11 \times 10^5$ | 0.43 |
| 8 | 0 | 1,000 | $3 \times 10^6$ | $2 \times 10^6$ | 0.20 |
| 9 | 1.5% AB | 1,000 | $3 \times 10^6$ | <10 | >5.47 |
| 10 | 1.5% AB | 2,000 | $3 \times 10^6$ | $4 \times 10^2$ | 3.87 |
| 11 | 1.5% AB | 3,000 | $3 \times 10^6$ | $33 \times 10^3$ | 1.95 |
| 12 | 1.5% AB | 4,000 | $3 \times 10^6$ | $2 \times 10^5$ | 1.37 |
| 13 | 1.5% AB | 5,000 | $3 \times 10^6$ | $3 \times 10^5$ | 1.07 |
| 14 | 1.5% AB | 6,000 | $3 \times 10^6$ | $5 \times 10^5$ | 0.97 |
| 15 | 0 | 1,000 | $3 \times 10^6$ | $16 \times 10^5$ | 0.30 |

EXAMPLE 7

Effect of Third Polymer on MS-2 Removal

This example evaluates the performance of filtration media including polyethylenimine containing polymer (polymer C) in addition to the presence of polymers A and B. The glass fiber used was grade 151 from Ahlstrom Technical Papers. The technique for providing the polymer on the glass fiber was provided according to the technique described in Example 2. The test was run at a flow rate of 1,000 ml/min through two layers of filtration media to provide a contact time of 0.033 seconds. The results of this example are reported in Table 7.

TABLE 7

The Effect of Third Polymer MS-2 Adsorption

| Sample Number | Solids Concentration and Polymer | Volume Filtered (ml) | MS-2 (PFU/ml) In | MS-2 (PFU/ml) Out | Log Reduction |
|---|---|---|---|---|---|
| 1 | 1.5% AB | 1,000 | $6 \times 10^5$ | $5 \times 10^1$ | 4.08 |
| 2 | 1.5% AB | 2,000 | $6 \times 10^5$ | $1.7 \times 10^3$ | 2.55 |
| 3 | 1.5% AB | 3,000 | $6 \times 10^5$ | $2.0 \times 10^4$ | 1.48 |
| 4 | 1.5% AB | 4,000 | $6 \times 10^5$ | $3.0 \times 10^5$ | 0.30 |
| 5 | 1.5% AB + 1.0% C | 1,000 | $6 \times 10^6$ | $2 \times 10^1$ | 5.48 |
| 6 | 1.5% AB + 1.0% C | 2,000 | $6 \times 10^6$ | $4 \times 10^2$ | 4.18 |
| 7 | 1.5% AB + 1.0% C | 3,000 | $6 \times 10^6$ | $3 \times 10^3$ | 3.30 |
| 8 | 1.5% AB + 1.0% C | 4,000 | $6 \times 10^6$ | $1 \times 10^4$ | 2.78 |
| 9 | 1.5% AB + 1.5% C | 1,000 | $6 \times 10^6$ | <10 | >5.78 |
| 10 | 1.5% AB + 1.5% C | 2,000 | $6 \times 10^6$ | $6 \times 10^2$ | 4.0 |
| 11 | 1.5% AB + 1.5% C | 3,000 | $6 \times 10^6$ | $1 \times 10^3$ | 3.78 |
| 12 | 1.5% AB + 1.5% C | 4,000 | $6 \times 10^6$ | $4 \times 10^3$ | 3.18 |

Heloxy 67 diepoxide from Shell Oil Co. was used to cross link the polyethylenine grade FG (molecular weight 800) from BASF with the glass fiber. The coating solution of 5% by wt. concentration of polymer C provides substantially no change in liquid flow through the filtration media while improving the microorganism removal capacity significantly.

It is believed that the low molecular weight of polymer C is advantageous because of its low viscosity and its ability to provide additional charge contribution on the filtration media without significantly reducing flow through the filtration media.

EXAMPLE 8

Bacteria Removal by the Charged Filter

This example demonstrates the effectiveness of the filtration media of the invention for absorbing bacteria. The test organism used for assessment of removal were, K.t., *Klebsiella terrigena* (ATCC-33257), E.c., *E. coli* (ATCC-15597) and B.d., *Brevundomas diminuta* (ATCC-1 1568). They were all prepared by overnight growth in LB broth (medium 1065 ATCC) to obtain the organism in the stationary growth phase. The average bacteria titer is around $1 \times 10^9$ CFU/ml. Microbial challenges of specific concentration were prepared by adding the fresh cultured bacteria to de-ionized water at pH 9.0.

Bacteria removed in the filtrant after passing through the filter were assayed by the colony counting method of a pour plate technique. 1 ml of filtrant is poured into a petri-dish and mixed with 5–10 ml tryptic soy agar (TSA) at a temperature not exceeding 45° C., which is then allowed to solidify in the plate. The pour plate is incubated at 37° C. overnight and the colonies counted and expressed as CFU (Colony Forming Unit) per ml. In adopting the enumeration method which uses colony counts, consideration should be given to the upper limit of the number of colonies produced on incubation. This limit should be such that each viable microorganism is able to express itself as a visible colony without being affected adversely by its near neighbors.

In order to have countable number of colonies formed in plate, the filtrants were sequentially diluted with 0.025 M Phosphate buffered saline (PBS) at pH 7.0 in 1:10 dilutions. The petri film aerobic count plate from 3M has also been used in assaying three different types of aerobic bacterium. The plate is a ready made culture medium system that contains standard nutrients, a cold water soluble gelling agent, and a tetrazolium indicator that facilitates colony enumeration. One ml samples are dispersed on the plate and the plate is incubated at 35° C. for 48 hours. The number of visible colonies will then be expressed in CFU/ml.

The filter media applied for bacteria removal utilizes a relatively open porosity of grade 164. Same procedure on cross-linking the polymers to grade 151 were applied to grade 164. Three different types of commonly known bacteria in water, Kt, Bd and Ec were dispersed in d.i. water at pH 9 as source of challenge respectively. The filtration was performed according to the conditions specified in Tables 8-1 through 8-3. After filtering a specific volume of bacteria containing water, the filtrants were collected in a test tube. All three different types of bacteria were assayed by mixing 1 ml of the diluted filtrant with 10 ml Tryptic soy agar (TSA) and following the pour plate assay procedure. The effectiveness of bacteria removal by the charge modified filter appear to depend more on the chemical structure interaction between the micro-organism and the cross-linked polymers other than their physical size. The better results for B.d. removal than for E.c. filtered under same condition can be explained as due to their surface chemistry properties toward the charges on filter surface. The importance of chemical functionality are further demonstrated between the mixed polymer AB vs. AB'. The AB' type show consistently better results then that of AB type. Once the amount and the type of chemistry were optimized, the increasing of contact time by either increasing the number of filter layers or decreasing the flow rate plays another dominating role in microorganism removal efficiency. The favorable flow kinetics with contract time less than one second to have more than 6 logs of bacteria reduction are achieved by using AB' polymers coating on glass matrix of 164 grade.

Glass fiber used in this example is grade 164 from Ahlstrom Technical Papers. The results of this example are reported in Tables 8-1, 8-2, and 8-3 for K.t., E.c., and B.d., respectively. This example demonstrates the effectiveness of the filtration media of the invention for removing different species of bacteria from water.

Polymer B' is a tertiary amine based epoxide type polymer formed by polymerizing methyl bis (3-amino propyl amine) (MBAPA) with dicarboxylic acid as described in U.S. Pat. Nos. 4,537,657 and 4,501,862.

TABLE 8-1

Bacteria Adsorption Variable Study on *B.d.*

| Solids Concentration and Polymer | No. of Layers | Flow Rate (ml/min) | Contact Time (sec) | Volume Filtered (ml) | *B.d.* Bacteria In ($n_0$) | (CFU/ml) Out ($N_t$) | Log Reduction |
|---|---|---|---|---|---|---|---|
| 1.5% AB | 1.0 | 50 | 0.58 | 100 | $1.4 \times 10^8$ | $2 \times 10^1$ | 6.84 |
| 1.5% AB | 1.0 | 50 | 0.58 | 200 | $1.4 \times 10^8$ | $29 \times 10^1$ | 5.68 |
| 1.5% AB | 1.0 | 50 | 0.58 | 500 | $1.4 \times 10^8$ | $3 \times 10^3$ | 4.84 |
| 1.5% AB' | 1.0 | 50 | 0.58 | 100 | $1.4 \times 10^8$ | $1 \times 10^1$ | 7.14 |
| 1.5% AB' | 1.0 | 50 | 0.58 | 200 | $1.4 \times 10^8$ | $2 \times 10^1$ | 6.84 |
| 1.5% AB' | 1.0 | 50 | 0.58 | 500 | $1.4 \times 10^8$ | $4 \times 10^1$ | 6.54 |
| 1.5% AB | 2.0 | 100 | 0.58 | 100 | $1.4 \times 10^8$ | <10 | >7.14 |
| 1.5% AB | 2.0 | 100 | 0.58 | 200 | $1.4 \times 10^8$ | $1 \times 10^1$ | 7.14 |
| 1.5% AB | 2.0 | 100 | 0.58 | 500 | $1.4 \times 10^8$ | $8 \times 10^1$ | 6.24 |
| 1.5% AB' | 2.0 | 100 | 0.58 | 100 | $1.4 \times 10^8$ | <10 | >7.14 |
| 1.5% AB' | 2.0 | 100 | 0.58 | 200 | $1.4 \times 10^8$ | <10 | >7.14 |
| 1.5% AB' | 2.0 | 100 | 0.58 | 500 | $1.4 \times 10^8$ | <10 | >7.14 |

TABLE 8-2

Bacteria Adsorption Variable Study on *K.t.*

| Solids Concentration and Polymer | No. of Layers | Flow Rate (ml/min) | Contact Time (sec) | Volume Filtered (ml) | *K.t.* Bacteria In ($n_0$) | (CFU/ml) Out ($N_t$) | Log Reduction |
|---|---|---|---|---|---|---|---|
| 1.5% AB | 1.0 | 50 | 0.58 | 100 | $23 \times 10^6$ | $24 \times 10^3$ | 2.98 |
| 1.5% AB | 1.0 | 50 | 0.58 | 200 | $23 \times 10^6$ | $89 \times 10^3$ | 2.41 |
| 1.5% AB | 1.0 | 50 | 0.58 | 500 | $23 \times 10^6$ | $48 \times 10^4$ | 1.68 |
| 1.5% AB' | 1.0 | 50 | 0.58 | 100 | $23 \times 10^6$ | $14 \times 10^1$ | 5.21 |
| 1.5% AB' | 1.0 | 50 | 0.58 | 200 | $23 \times 10^6$ | $12 \times 10^2$ | 4.28 |
| 1.5% AB' | 1.0 | 50 | 0.58 | 500 | $23 \times 10^6$ | $20 \times 10^3$ | 3.06 |
| 1.5% AB | 2.0 | 100 | 0.58 | 100 | $23 \times 10^6$ | <10 | >6.2 |
| 1.5% AB | 2.0 | 100 | 0.58 | 200 | $23 \times 10^6$ | <10 | >6.2 |
| 1.5% AB | 2.0 | 100 | 0.58 | 500 | $23 \times 10^6$ | $17 \times 10^1$ | 5.13 |
| 1.5% AB' | 2.0 | 100 | 0.58 | 100 | $23 \times 10^6$ | <10 | >7.0 |
| 1.5% AB' | 2.0 | 100 | 0.58 | 200 | $23 \times 10^6$ | <10 | >7.0 |
| 1.5% AB' | 2.0 | 100 | 0.58 | 500 | $23 \times 10^6$ | $2 \times 10^1$ | 6.06 |

TABLE 8-3

Bacteria Adsorption Variable Study on *E.c.*

| Solids Concentration and Polymer | No. of Layers | Flow Rate (ml/min) | Contact Time (sec) | Volume Filtered (ml) | *E.c.* Bacteria In ($n_0$) | (CFU/ml) Out ($N_t$) | Log Reduction |
|---|---|---|---|---|---|---|---|
| 1.5% AB | 2 | 100 | 0.58 | 500 | $1 \times 10^7$ | $1 \times 10^3$ | 4.0 |
| 1.5% AB | 2 | 100 | 0.58 | 1000 | $1 \times 10^7$ | $5 \times 10^4$ | 2.3 |
| 1.5% AB | 2 | 100 | 0.58 | 1500 | $1 \times 10^7$ | TNTC* | <1 |
| 1.5% AB | 2 | 100 | 0.58 | 2000 | $1 \times 10^7$ | TNTC | <1 |
| 1.5% AB' | 2 | 100 | 0.58 | 500 | $1 \times 10^7$ | $1 \times 10^1$ | 6.0 |
| 1.5% AB' | 2 | 100 | 0.58 | 1000 | $1 \times 10^7$ | $9 \times 10^2$ | 4.05 |
| 1.5% AB' | 2 | 100 | 0.58 | 1500 | $1 \times 10^7$ | $2 \times 10^4$ | 2.70 |
| 1.5% AB' | 2 | 100 | 0.58 | 2000 | $1 \times 10^7$ | $17 \times 10^4$ | 1.77 |
| 3% AB | 2 | 100 | 0.58 | 500 | $1 \times 10^7$ | $4 \times 10^3$ | 3.40 |
| 3% AB | 2 | 100 | 0.58 | 1000 | $1 \times 10^7$ | $18 \times 10^4$ | 1.75 |
| 3% AB | 2 | 100 | 0.58 | 1500 | $1 \times 10^7$ | TNTC | <1 |
| 3% AB | 2 | 100 | 0.58 | 2000 | $1 \times 10^7$ | TNTC | <1 |
| 3% AB' | 2 | 100 | 0.58 | 500 | $1 \times 10^7$ | $1 \times 10^1$ | 6.0 |
| 3% AB' | 2 | 100 | 0.58 | 1000 | $1 \times 10^7$ | $1 \times 10^2$ | 5.0 |
| 3% AB' | 2 | 100 | 0.58 | 1500 | $1 \times 10^7$ | $5 \times 10^3$ | 3.3 |
| 3% AB' | 2 | 100 | 0.58 | 2000 | $1 \times 10^7$ | $27 \times 10^3$ | 2.50 |
| 3% AB' | 3 | 100 | 0.87 | 500 | $1 \times 10^7$ | <10 | >6.0 |
| 3% AB' | 3 | 100 | 0.87 | 1000 | $1 \times 10^7$ | <10 | >6.0 |
| 3% AB' | 3 | 100 | 0.87 | 2000 | $1 \times 10^7$ | <10 | >6.0 |

*TNTC means too numerous to count

EXAMPLE 9

Effect of Charge Density on Microorganism Removal

The charge interaction between the chemical functional groups on the filtration media and the surface of the microorganism is considered a major force for removing microorganisms from the water. Therefore, the virus adsorptivity by the filter is expected to be directly related to the available charge density provided on the filtration media. The higher the charge density, the higher the number of charged groups available for microorganism adsorption. The charge density of polymers A and B are 3 milli-equivalent per gram according to the polymer supplier. The estimated charge density per gram of filtration media are calculated and reported in Table 9 based upon the weight of polymer reacted on the media. In order to correlate the charge density with the microorganism removal capacity, we adopted the microorganism removal coefficiency as an index number. 151 glass fiber and polymeric AB mixture in different charge density at 100 ml/min. In this example, the data is taken from example 4. The MS-2 removal coefficient calculated based on the above number are tabulated in Table 9 and expressed in ml/g-sec. The relationship between the charge density and MS-2 removal coefficient is shown in Table 9. It is believed that the decrease in virus removal coefficient with increasing volume of virus containing water passing through the filtration media is due to the gradual loss of active sites occupied by virus adsorption. The high charge density with more active groups are available for capturing the virus show less reduction in removal coefficient. The microorganism removal coefficient calculated based upon filter weight, contact time, volume filtered and microorganism concentration serves as a valuable index for identifying the extent of chemical functional groups provided in the filtration media.

TABLE 9

The effect of charge density on Virus Adsorptivity

| Sample Number | Solids Concentration and Polymer | % Coating Weight Gain | Weight of Filtration Media | Charge Density (milli-equiv./g) | Volume Filtered (ml) | Virus Removal Coefficient |
|---|---|---|---|---|---|---|
| 1 | 1.5% AB | 8.0% | 0.173 g | 0.24 | 1,000 | $9.21 \times 10^5$ |
| | | | | | 2000 | $8.7 \times 10^5$ |
| | | | | | 4000 | $6.7 \times 10^5$ |
| 2 | 2.0% AB | 10.6% | 0.177 g | 0.32 | 1,000 | $1.06 \times 10^6$ |
| | | | | | 2,000 | $1.03 \times 10^6$ |
| | | | | | 4,000 | $9.45 \times 10^5$ |
| 3 | 2.5% AB | 13.33% | 0.181 g | 0.40 | 1,000 | $1.39 \times 10^6$ |
| | | | | | 2,000 | $1.34 \times 10^6$ |
| | | | | | 4,000 | $1.19 \times 10^6$ |
| 4 | 3.0% AB | 16.0% | 0.186 g | 0.48 | 1,000 | $3.46 \times 10^6$ |
| | | | | | 2,000 | $3.23 \times 10^6$ |
| | | | | | 4,000 | $3.19 \times 10^6$ |

A useful index of microorganism removal coefficient is adapted from Kawabata, et al., *Applied and Environmental Microbiology* 46, pages 203–210, 1983. This index is available to evaluate the effectiveness of the filter on microorganism removal. As can be seen in the previous examples, the relation of the logarithm of viral microorganism counts to contact time can be characterized as generally linear in the early stage of contact which indicates the process follows first order rate. Thus, we define the removal coefficient as follows:

$$\text{Removal Coefficient} = \frac{V}{Wt}\log\frac{N_o}{N_t}$$

Where $N_0$ is the initial number of microorganisms counts expressed in CFU/ml for bacteria and PFU/ml for MS-2 virus, N, is the number of counts at contact line t, V is the volume filtered, W is the dry weight of filter material applied in filtration, and t is the contact time which are roughly estimated from the total volume of filter material divided by the flow rate and by assuming 50% porosity in filters.

The MS-2 removal coefficient is calculated by passing 1 to 4 liters of water at pH 9 containing $1.8 \times 10^6$ PFU/ml of MS-2 through one layer of filtration media prepared from

EXAMPLE 10

Effect of Type No. 2 Water on Microorganism Removal

In order to satisfy the performance requirements of a "microbiological water purifier," filtration media were tested in test water type No. 2 according to the "Guide Standard and Protocol for Testing Microbiological Water Purifiers" published by EPA in 1987. This water is intended for the stressed challenge phase of testing where units involve halogen disinfectant and was constituted with chemical and physical characteristics as follows:

(a) Free of chlorine or other disinfectant residual;

(b) pH 9.0±0.2;

(c) Total organic carbon (TOC) at 10 mg/l by adding humic acid;

(d) Turbidity at 30 NTU by adding A.C. dust particles; and (e) Total dissolved solid (TDS) 1,500 mg/l by adding sea salt.

The test was run similar to example 1 except for the use of a PUR® Hiker™ filter cartridge available from Recovery Engineering, Inc. as a pre-filter to avoid premature clogging caused by the A.C. fine dust particles. The granular activated carbon in the pre-filter was removed for this test. The interference caused by the added TOC and TDC in type no. 2 water on efficiency of microorganism reduction is quite obvious from the testing results. An additional layer of filter media has to be added in order to compensate the loss of charge sites or charge weakening due to the presence of sea salt and humic acid in EPA specified type 2 test water.

TABLE 10

MS-2 Virus Adsorption in EPA Type No. 2 Water

| Sample Number | Solids Concentration and Polymer | No. of Layers | Flow Rate (ml/min) | Volume Filter (ml) | MS-2 (PFU/ml) In ($n^0$) | MS-2 (PFU/ml) Out ($N_t$) | Log Reduction |
|---|---|---|---|---|---|---|---|
| 1 | 6% B | 3.0 | 40.0 | 1,000 | $2 \times 10^9$ | $3 \times 10^2$ | 6.8 |
| 2 | 6% B | 3.0 | 500.0 | 2,000 | $2 \times 10^9$ | $2 \times 10o^4$ | 5.0 |
| 3 | 6% B | 4.0 | 40.0 | 3,000 | $2 \times 10^9$ | $4 \times 10^2$ | 6.7 |
| 4 | 6% B | 4.0 | 500.0 | 4,000 | $2 \times 10^9$ | $1 \times 10^5$ | 4.3 |
| 5 | 1.5% A then 1.5% B | 4.0 | 150.0 | 1,000 | $2 \times 10^9$ | <10 | >8.3 |
| 6 | 1.5% A then 1.5% B | 4.0 | 1,600. at 20 PSI | 1 gallon | $2 \times 10^9$ | $2 \times 10^3$ | 5.0 |
| 7 | 1.5% A then 1.5% B | 4.0 | 1,800. at 25 PSI | 2 gallons | $2 \times 10^9$ | $4 \times 10^4$ | 3.7 |
| 8 | 6% AB | 4.0 | 80.0 | 1,000 | $3 \times 10^8$ | $6 \times 10^1$ | 6.7 |
| 9 | 6% AB | 4.0 | 200.0 | 2,000 | | $4 \times 10^1$ | 6.8 |
| 10 | 6% AB | 4.0 | 280.0 | 3,000 | | $3 \times 10^1$ | 7.0 |
| 11 | 6% AB | 4.0 | 250.0 | 4,000 | | $3 \times 10^1$ | 7.0 |

The humic acid in type 2 water was found to be also adsorbed by the filter matrix. The competitive adsorption of both humic acid and virus toward the charge sites in the filter results in reduction in virus adsorption capacity, as shown in Table 10. When we observe the loss of 2 log reduction in MS-2 removal by three layers of filter media in samples 1 and 2. An additional layer was added to compensate the loss of charge sites due to humic acid adsorption. The added charge sites raised the MS-2 adsorption efficiency back to 6.7 log reduction in sample 3, but again it starts to show efficiency reduction caused by the presence of 10 ppm humic acid in type 2 water. Sample 5–7 demonstrate the using of combined A and B polymers for MS-2 adsorption in the presence of humic acid as competing molecules. Only through the use of A and B mixed polymer at higher concentration, we will be able to provide sufficient number of charge sites to satisfy the adsorption for both humic acid and microorganisms, as shown in Samples 8 to 11.

EXAMPLE 11

Effect of Cross-Linking Reaction on Filter Extractables

Filtration media were tested by extraction tests to evaluate the amount of polymer which leaves the filtration media. The extraction tests were performed by soaking two grams of filtration media in 250 ml nitrogen free water for two hours at room temperature. A sample of extractant was digested using the persulfate method as described in "standard method for the examination of water and waste water," edited by Eaton et al., Apha, Washington, D.C. The method utilizes alkaline oxidation at 100° C. to 110° C. to convert nitrogen to nitrate. Total nitrogen is then determined by analyzing the nitrate using a Hach DR-700 calorimeter. The results are expressed as amount of nitrogen (ppm) in extracted water. The filtration media tested are identified below and in Table 11. The amount of nitrogen provided as a result of the extraction tests for each filtration media is provided in Table 11.

TABLE 11

Nitrogen Analysis on Extractables from Filtration Media

| Sample Number | Solids Concentration and Polymer | Weight Gain after Coating | Formation of Chemical Bond | Extracts from Nitrogen Analysis (ppm) |
|---|---|---|---|---|
| 1 | 3% AB' | 16% | Yes | 8.5 |
| 2 | 1.5% AB' | 8% | Yes | 6.2 |
| 3 | 3.0% B' | 18% | Yes | 10.5 |
| 4 | 3.0% modified B' | 18% | No | 55.0 |
| 5 | 3.0% PEI | 17% | No | 90.0 |
| 6 | 3.0% modified A | 17% | No | 87.1 |

All filtration media were prepared from grade 151 glass fiber available from Ahlstrom Technical Papers. The glass media was dipped into a polymer bath having the weight percent solids identified in Table 11. When two polymers were provided in the polymer bath, the polymers were provided at a weight ratio of 1:1. Sample number one was prepared from a polymer bath including 3% by weight polymer A and polymer B'. Sample number 2 was prepared from a polymer bath including 1.5 wt. % polymer A and polymer B'. Sample number 3 was prepared from a polymer bath including 3.0 wt. % polymer B'. Sample number 4 was prepared from a polymer bath including 3.0 wt. % of a polymer similar to B' but without azitidium groups. Sample number 5 was prepared from a polymer bath including 3.0 wt. % polyethylenimine. Sample number 6 was prepared from a polymer bath including 3.0 wt. % of a polymer similar to polymer A but without azitidium groups. The filtration media were dried and cured at a temperature of 300° F. for six minutes. In the case of sample numbers 4–6, it is believed that the polymers did not react to the glass fiber. In contrast, it is believed that the polymers in sample numbers 1–3 did react to the glass fiber by covalent bond.

It is observed from the data in Table 11 that the combination of polymers show extractables which are less than the single polymer. It is believed that this may be the result of a reaction between the polymers. Sample numbers 4–6 provide a level of nitrogen in the extract which averages over ten times higher than the levels provided by sample numbers 1–3.

The extractables or leachables from the filter media are the functions of polymer concentrations, the type of cross-linker in polymer structure as well as the conditions of cross-linking. Polymers without a cross-linker are also expected to be adsorbed on glass fiber surface simply through charge interactions only without forming covalent-bond, especially when the silica on glass fiber surface are ionized in alkaline conditions.

EXAMPLE 12

Pour-Through Filter

In this example, a standard pour-through type filter (PUR Plus produced by Recovery Engineering, Inc) was modified and tested. The filter contains a pleated non-woven glass media, similar to the Ahlstrom 164 cited in earlier examples, except that the media has a more open porosity, a binder, and laminated outer layers. This media was treated with 1.5% AB polymer mixture in the manner as before. In sample number 1, two pleated polymer treated filtration medias were assembled in series in the filter. This filter is tested by filling the upper reservoir with 1.25 liters of challenge water, and collecting a sample of the water after 1 liter has passed through the filter. This first liter requires approximately 5 minutes to pass through the filter, which is a typical rate of flow for this type of product in the market. The above results show that it is possible to remove virus in a pour-through device with typical flow rates and, while one layer is enough to achieve low level removal, two layers produces a much higher removal level.

TABLE 2

| Sample | No. Pleated | Volume | MS-2 (PFU/ml) | | Log |
|---|---|---|---|---|---|
| No. | Layers | Filtered (liters) | Influent | Effluent | Reduction |
| 1 | 2 | 1 | | <10 | >4.5 |
| | | 2 | | <10 | >4.5 |
| 2 | 1 | 0.5 | $3.0 \times 10^5$ | 8000 | 1.6 |
| | | 1 | | 100 | 3.5 |
| 3 | 1 | 0.5 | | 80 | 3.6 |
| | | 1 | | 400 | 2.9 |

EXAMPLE 13

Faucet Mount Filter

In this example, a faucet-mount type filter (PUR Plus produced by Recovery Engineering, Inc.) was modified and tested. The filter contains a molded filter element consisting primarily of powdered activated carbon. This element is normally 2" outer diameter, with a ⅝" inner diameter and 2.5" long (right circular cylinder with a hole in the middle). The filter element was modified to have an outer diameter of 1.82 inches and then wrapped with a 24" long, 2.5" wide piece of 151 media treated with 1.5% AB resin. This wraps the block with four layers of the virus removal media. This filter is tested by pumping water at pH 9.0 with viruses through the filter at 60 psi. The table above summarizes the conditions and results. The results show the ability of a practical faucet mount filter to remove viruses in water even at very high concentrations (test 1 and 2). When the concentration is dropped (test 3), the capacity of the filter is very high, showing no sign of breakthrough after 80 gallons.

TABLE 13

| Test | Flow Rate | Volume | MS-2 (PFU/ml) | | Log |
|---|---|---|---|---|---|
| No. | (lpm) | Filtered (gal.) | Influent | Effluent | Reduction |
| | | 0.26 | | <10 | >5.6 |
| | | 1 | | <10 | >5.6 |
| | | 2 | | <10 | >5.6 |
| 1 | 2.8 | 3 | $4.0 \times 10^6$ | <10 | >5.6 |
| | | 4 | | <10 | >5.6 |
| | | 5 | | <10 | >5.6 |
| | | 6 | | 830 | 5.4 |
| | | 7 | | 1300 | 5.2 |
| 2 | 2.8 | 8 | $2.0 \times 10^8$ | 1700 | 5.1 |
| | | 9 | | 1000 | 5.3 |
| | | 10 | | 1000 | 5.3 |
| | | 5 | | <10 | >3.5 |
| | | 10 | | <10 | >3.5 |
| 3 | 2.73 | tested every 5 gallons to | $3.0 \times 10^4$ | | |
| | | 80 | | <10 | >3.5 |

The above specification, examples and data provide a complete description of the manufacture and use of the composition of the invention. Since many embodiments of the invention can be made without departing from the spirit and scope of the invention, the invention resides in the claims hereinafter appended.

What is claimed:

1. A filter for removing microorganisms from a liquid, comprising:

a filtration media comprising a substrate having a reactive surface and at least a first and second cationic polymer bonded to the reactive surface of said substrate, each of said cationic polymers including a plurality of cationic groups so that said filtration media has a cationic charge for attracting microorganisms in a liquid, wherein said first and second cationic polymers are mixed prior to bonding to said reactive surface;

wherein said first cationic polymer is a polyamide-polyamine polymer having the following repeating units;

I

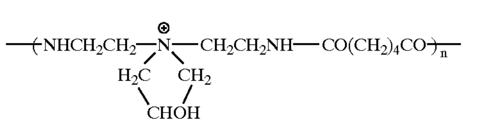

wherein n is between about 10 and about 100,000; and wherein said second cationic polymer is at least one of a polyamine polymer having the following repeating units:

II

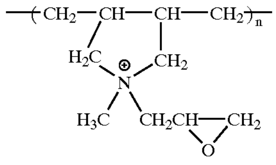

wherein n is between about 10 and about 100,000 and a polyamide-polyamine polymer having the following repeating units:

III

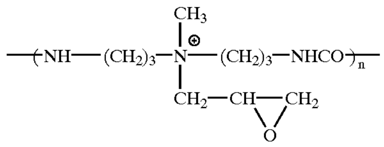

wherein n is between about 10 and about 100,000.

2. A filter for removing microorganisms from a liquid according to claim 1, wherein said second cationic polymer is said polyamine polymer.

3. A filter for removing microorganisms from a liquid according to claim 1, wherein said second cationic polymer is a polyamide-polyamine.

4. A filter for removing microorganisms from a liquid according to claim 1, wherein said filtration media includes a charge density of at least about 0.001 milliequivalent/gram filtration media.

5. A filter for removing microorganisms from a liquid according to claim 1, wherein said substrate comprises at least one of glass, silica, alumina, polystyrene, polypropylene, polyethylene, polyvinyl alcohol, polyamide, cellulose, and mixtures thereof.

6. A filter for removing microorganisms from a liquid according to claim 1, wherein said substrate comprises glass fiber.

7. A filter for removing microorganisms from a liquid according to claim 1, wherein the filtration media exhibits an extractables of less than 20 ppm nitrogen in extracted water, wherein the extractables is determined by after soaking 2 g of filtration media in 250 ml nitrogen free water for two hours at room temperature.

8. The filter of claim 1, further in combination with a housing having an inlet, an outlet, an interior region containing said filtration media, a valve for controlling flow water into said inlet of said housing, and an adapter for attaching said valve to a faucet.

9. The combination of claim 8, wherein said valve comprises a first outlet in fluid connectivity with said inlet of said housing and a second outlet for bypassing said filtration media.

10. The combination of claim 8, further comprising a carbon block cylinder having an exterior cylindrical surface and an interior cylindrical surface.

11. The combination of claim 10, wherein said filtration media is provided adjacent said exterior cylindrical surface of said carbon block cylinder.

12. The combination of claim 10, wherein said filtration media is provided adjacent said interior cylindrical surface of said carbon block cylinder.

13. The combination of claim 12, further comprising a porous tube supporting said filtration media provided on said interior cylindrical surface of said carbon block cylinder.

14. The filter of claim 1, further in combination with a housing having an inlet, an outlet, and an interior region, wherein said filtration media is pleated and is disposed within said interior region of said housing.

15. The combination of claim 14, further comprising activated carbon disposed within said Interior region.

16. The combination of claim 14, further comprising an ion exchange resin disposed within said interior region.

17. A filter for removing microorganisms from a liquid according to claim 1, further comprising a third cationic polymer reacted to said substrate.

18. A filter for removing microorganisms from a liquid according to claim 17, wherein the third cationic polymer is a polyamine having the following repeating units:

$$-\!\left(CH_2-CH_2-NH\right)_n\!-$$ IV wherein n of the formula IV is between about 10 and about 1,000,000 and wherein a cross-linking agent is reacted with the third cationic polymer and the substrate.

19. A filter for removing microorganisms from a liquid according to claim 17, wherein said third cationic polymer is polyethylenimine.

20. A filter for removing microorganisms from a liquid according to claim 17, wherein the weight ratio of the first and second cationic polymers to said third cationic polymer is between about 9:1 and about 1:9.

21. A filter for removing microorganisms from a liquid according to claim 17, wherein the weight ratio of said first and second cationic polymers to said third cationic polymer is between about 3:1 and about 1:1.

22. A filter for removing microorganisms from a liquid according to claim 17, wherein said third cationic polymer is reacted with said substrate after said mixture of said first and second polymers.

23. A filter for removing microorganisms from a liquid according to claim 17, wherein the molecular weight of said third cationic polymer is between about 300 and about 1,000,000.

24. A filter for removing microorganisms from a liquid according to claim 1, wherein the weight ratio of said first cationic polymer to said second cationic polymer Is between about 1:9 to about 9:1.

25. A filter for removing microorganisms from a liquid according to claim 1, wherein the weight ratio of said first cationic polymer to said second cationic polymer is between about 1:2 to about 2:1.

26. A filter for removing microorganisms from a liquid according to claim 1, wherein said filtration media exhibits a MS-2 virus removal coefficient in water of greater than 10mL/g-sec.

* * * * *